(12) United States Patent
Rouru et al.

(10) Patent No.: US 10,857,120 B2
(45) Date of Patent: Dec. 8, 2020

(54) USE OF LEVODOPA, CARBIDOPA AND ENTACAPONE FOR TREATING PARKINSON'S DISEASE

(71) Applicant: ORION CORPORATION, Espoo (FI)

(72) Inventors: Juha Rouru, Turku (FI); Mikko Kuoppamäki, Raisio (FI); Juha Ellmen, Turku (FI); Pekka Männistö, Helsinki (FI)

(73) Assignee: ORION CORPORATION, Espoo (FI)

( * ) Notice: Subject to any disclaimer, the term of this patent is extended or adjusted under 35 U.S.C. 154(b) by 944 days.

(21) Appl. No.: 14/504,925

(22) Filed: Oct. 2, 2014

(65) Prior Publication Data

US 2015/0150839 A1   Jun. 4, 2015

Related U.S. Application Data

(63) Continuation of application No. 13/582,427, filed as application No. PCT/FI2011/000013 on Mar. 3, 2011, now abandoned.

(60) Provisional application No. 61/438,416, filed on Feb. 1, 2011, provisional application No. 61/412,821, filed on Nov. 12, 2010, provisional application No. 61/310,398, filed on Mar. 4, 2010.

(51) Int. Cl.
*A61K 31/277* (2006.01)
*A61K 45/06* (2006.01)
*A61K 9/28* (2006.01)
*A61K 31/198* (2006.01)
*A61K 31/165* (2006.01)
*A61K 31/4439* (2006.01)
*A61K 9/20* (2006.01)

(52) U.S. Cl.
CPC ............ *A61K 31/277* (2013.01); *A61K 9/286* (2013.01); *A61K 31/165* (2013.01); *A61K 31/198* (2013.01); *A61K 31/4439* (2013.01); *A61K 45/06* (2013.01); *A61K 9/2077* (2013.01)

(58) Field of Classification Search
CPC ....................................................... A61K 31/33
USPC .................................................. 514/183, 170
See application file for complete search history.

(56) References Cited

U.S. PATENT DOCUMENTS

| 5,135,950 | A | 8/1992 | Pippuri et al. |
| 5,236,952 | A | 8/1993 | Bernauer et al. |
| 5,607,969 | A | 3/1997 | Milman et al. |
| 6,500,867 | B1 | 12/2002 | Virkki et al. |
| 2003/0017201 | A1 | 1/2003 | Virkki et al. |
| 2004/0166159 | A1 | 8/2004 | Han et al. |
| 2006/0013875 | A1 | 1/2006 | Han et al. |
| 2011/0310398 | A1 | 12/2011 | Okano et al. |

FOREIGN PATENT DOCUMENTS

| EP | 0 237 929 | 9/1987 |
| EP | 0 309 827 | 4/1989 |
| GB | 940 596 | 10/1963 |
| JP | 2009-544571 | 12/2009 |
| WO | WO 00/37423 | 6/2000 |
| WO | WO 2004/052841 | 6/2004 |
| WO | WO 2005/063696 | 7/2005 |
| WO | WO 2005/121069 | 12/2005 |
| WO | WO 2006/037061 | 4/2006 |
| WO | WO 2006/131591 | 12/2006 |
| WO | WO 2007/010085 | 1/2007 |
| WO | WO 2007/013830 | 2/2007 |
| WO | WO 2007/067495 | 6/2007 |
| WO | WO 2008/053297 | 5/2008 |
| WO | WO 2009/108077 | 9/2009 |
| WO | WO 2010/020969 | 2/2010 |
| WO | WO 2010/020970 | 2/2010 |
| WO | WO 2010/027340 | 3/2010 |
| WO | WO 2010/108845 | 9/2010 |

OTHER PUBLICATIONS

Ahtila, S., et al: "Effect of Entacapone, A COMT Inhibitor, on the Pharmacokinetics and Metabolism of Levodopa After Administration of Controlled-Release Levodopa-Carbidopa in Volunteers", Clinical Neuropharmacology, Raven Press, New York, NY, US, vol. 18, No. 1, Feb. 1, 1995 (Feb. 1, 1995), pp. 46-57.

(Continued)

*Primary Examiner* — Layla Soroush
(74) *Attorney, Agent, or Firm* — Finnegan, Henderson, Farabow, Garrett & Dunner, L.L.P.

(57) ABSTRACT

The present disclosure provides a method for the treatment of Parkinson's disease comprising simultaneously or sequentially administering to a patient in need of treatment of Parkinson's disease a dosage form comprising (i) levodopa in an amount ranging from 50 mg to 300 mg,
(ii) carbidopa in an amount ranging from 25 mg to 150 mg or a therapeutically equivalent amount of another aromatic amino acid decarboxylase inhibitor, and
(iii) entacapone in an amount ranging from 50 mg to 300 mg, wherein the proportion of entacapone to carbidopa in said dosage form ranges from 0.3:1.0 to 3.2:1.0 by weight, a moderately potent COMT inhibitor in an amount ranging from 25 mg to 200 mg, wherein the proportion of said COMT inhibitor to carbidopa in said dosage form ranges from 0.16:1.0 to 3.08:1.0 by weight, or a highly potent COMT Inhibitor in an amount ranging from 1 mg to 100 mg, wherein the proportion of said COMT inhibitor to carbidopa in said dosage form ranges from 0.006:1.0 to 1.54:1.0 by weight.

Pharmaceutical dosage forms used in said methods are also disclosed.

26 Claims, 3 Drawing Sheets

(56) References Cited

OTHER PUBLICATIONS

Eggert, K., et al. "Direct switch from levodopa/benserazide or levodopa/carbidopa to levodopa/carbidop/entacapone in Parkinson's disease patients with wearing off: efficacy, safety and feasibility an open-label, 6-week study," *J. Neural Transmission* (2009) 117(3):333-342.

International Search Report for PCT/FI2011/000013 dated Sep. 12, 2011.

Novartis: "Stavelo", Apr. 1, 2008, Apr. 1, 2008, pp. 1-26.

Pahwa R et al: "Levodopa-related wearing-off in Parkinson's disease: Identification and management", Current Medical Research and Opinion, Informa Healthcare, GB, vol. 25, No. 4, Jan. 1, 2009 (Jan. 1, 2009), pp. 841-849.

Heikkinen, H., et al. "Entacapone improves the availability of L-dopa in plasma by decreasing its peripheral metabolism independent of L-dopa/carbidopa dose," *J. Clin. Pharmacol.* (2002) 54:363-371.

Communication from the Eurpean Patent Office dated Jun. 8, 2015, regarding observations by a third party concerning the patentability of European Application No. 11 709446.6.

Cedarbaum, J. et al., "Effect of Supplemental Carbidopa on Bioavailability of I-Dopa," Clinical Neuropharmacology, Apr. 1986.

Eija Schultz et al., Determination of Catechol-O-Methyltransferase Activity in Erythrocytes by High Performance Liquid Chromatography with Electrochemical Detection, Biomedical Chromatography, vol. 3, No. 2, Mar. 1989, pp. 64-67.

Hitoshi Nohta at al., Assay for Catechol-O-Methyltransferase in Erythrocytes Using a New Fluorogenic Substrate, 2-(3,4-dihydroxyphenyl)naphto[1,2-d]thiazole, Journal of Chromatography, vol. 308. 1984, pp. 93-100.

T. Keränen et al., Inhibition of Soluble Catechol-O-Methyltransferase and Single-Dose Pharmacokinetics After Oral and Intravenous Administration of Entacapore. Eur. J. Clin. Pharmcol, vol. 46, Mar. 1994, pp. 151-157.

J. Dingemanse et al., Integrated Pharmacokinetics and Pharmacodynamics of the Novel Catechol-O-Methyltransferase Inhibitor Tolcapone During First Administration to Humans, Clin. Pharmacol. Ther., vol. 57, No. 5, 1995, pp. 508-517.

Pharmaceutical Dosage Forms and Drug Delivery Systems (Loyd V. Allen, Jr. et al. eds., 8th ed. 2005).

Handbook of Pharmaceutical Excipients (Raymond C. Rowe et al., eds., 6th ed. 2009).

Remington's Pharmaceutical Sciences (Alfonso R. Gennaro ed., 18th ed. 1990).

Handbook of Pharmaceutical Granulation Technology (Dilip M. Parikh ed., 2d ed. 2005).

Pharmaceutics, The Science of Dosage Form Design (Michael E. Aulton ed., 2d ed. 2002).

The Theory and Practice of Industrial Pharmacy (Leon Lachman et al. eds., 3d ed. 1986).

Communication from the European Patent Office dated Jan. 16, 2014, regarding observations by a third party concerning the patentability of European Application No. 11 709446.6.

Communication from the European Patent Office dated Mar. 20, 2014, regarding observations by a third party concerning the patentability of European Application No. 11 709446.6.

Communication from the European Patent Office dated Apr. 10, 2014, regarding observations by a third party concerning the patentability of European Application No. 11 709446.6.

Communication from the European Patent Office dated May 23, 2014, regarding observations by a third party concerning the patentability of European Application No. 11 709446.6.

Communication from the European Patent Office dated Mar. 21, 2016, regarding observations by a third party concerning the patentability of European Application No. 11 709446.6.

Boards of Appeal of the European Patent Office, Decision of May 4, 2000, Case No. T 0233/96—3.3.2., Application No. 8930396.2.

British National Formulary, vol. 60, Sep. 2010, pp. 300-304.

Stalevo® Label, rev. Feb. 2, 2009.

USE OF LEVODOPA, CARBIDOPA AND ENTACAPONE FOR TREATING PARKINSON'S DISEASE

This is a continuation of application Ser. No. 13/582,427, filed Sep. 2, 2012 (pending) which is a national stage application of International Application No. PCT/FI2011/000013, filed on Mar. 3, 2011, which claims the benefit of priority of U.S. Provisional Application Nos. 61/310,398, filed Mar. 4, 2010; 61/412,821, filed Nov. 12, 2010; and 61/438,416, filed on Feb. 1, 2011, all of which are incorporated herein by reference.

FIELD OF THE INVENTION

The present disclosure relates to a method for the treatment of Parkinson's disease as well as to pharmaceutical dosage forms used in said method.

BACKGROUND OF THE INVENTION

Levodopa ((−)-L-alpha-amino-beta-(3,4-dihydroxybenzene)propanoic acid) is a commonly used drug in the treatment of Parkinson's disease (PD). It is commercially available as a combination with an aromatic amino acid decarboxylase (AADC) inhibitor such as carbidopa ((−)-L-alpha-hydrazino-alpha-methyl-beta-(3,4-dihydroxybenzene)propionic acid)monohydrate) or benserazide hydrochloride (N-DL-seryl)-N'-(2,3,4-trihydroxy-benzyl) hydrazine hydrochloride). The combination of levodopa with carbidopa is sold under, for instance, the trademarks SINEMET®, DUODOPA® and PARCOPA® and the combination with benserazide hydrochloride is sold under, for instance, the trademark MADOPAR®.

Entacapone ((E)-2-cyano-3-(3,4-dihydroxy-5-nitrophenyl)-N-diethyl-2propenamide) is a catechol-O-methyl transferase (COMT) inhibitor that is used in combination with levodopa and carbidopa or benserazide to treat Parkinson's disease. It is commercially available as a stand-alone formulation under, for instance, the trademarks COMTESS® and COMTAN® and as a fixed combination (levodopa:carbidopa:entacapone: 50 mg:12.5 mg:200 mg, 75 mg:18.75 mg:200 mg, 100 mg:25 mg:200 mg. 125 mg:31.25 mg:200 mg, 150 mg:37.5 mg:200 mg and 200 mg:50 mg:200 mg) under, for instance, the trademark STALEVO®.

Typically, the proportion of levodopa to carbidopa (when calculated as anhydrate) or benserazide hydrochloride in commercial formulations is 4:1 (or sometimes also 10:1 with carbidopa) by weight and the proportion of entacapone to carbidopa or benserazide hydrochloride, respectively, is at least 4:1 by weight. None of the above-cited products nor any publication, of which applicants are aware, discloses the simultaneous or sequential administration of levodopa, carbidopa (or benserazide hydrochloride) and entacapone to a human in a repeated manner, wherein the proportion of entacapone to carbidopa is less than 4:1 by weight.

Tolcapone (3,4-dihydroxy-4'-methyl-5-nitro-benzophenone) is another COMT inhibitor that is used as a 100 mg or 200 mg stand-alone formulation administered three times daily as an adjunct to the levodopa/carbidopa or levodopa/benserazide treatment, the proportions of levodopa to the AADC inhibitor being the same as those used with entacapone. Tolcapone is sold under trademark TASMAR® and its preparation has been disclosed in EP 0 237 929.

WO 2007/013830 discloses several COMT inhibitors including BIA 9-1067 (5-[3-(2,5-dichloro-4,6-dimethyl-1-oxypyridin-3-yl)-[1,2,4]oxadiazol-5-yl]-3-nitrobenzene-1,2-diol), which is undergoing clinical evaluation. WO 2000/37423 discloses BIA 3-201 (1-(3,4-dihydroxy-5-nitrophenyl)-2-phenyl-ethanone, nebicapone).

WO 2007/010085 discloses new COMT inhibitor such as (3-chloro-5,6-dihydroxy-7-nitro-benzo[b]thiophen-2-yl)-morpholin-4-yl-methanone, 3-chloro-5,6-dihydroxy-7-nitro-benzo[b]thiophene-2-carboxylic acid diethylamide, (3-chloro-5,6-dihydroxy-7-nitro-benzo[b]thiophen-2-yl)-piperidin-1-yl-methanone, 3-chloro-5,6-dihydroxy-7-nitro-benzo[b]thiophene-2-carboxylic acid phenylamide, 3-[(3-chloro-5,6-dihydroxy-7-nitro-benzo[b]thiophene-2-carbonyl)-amino]-benzoic acid, 4-[(3-chloro-5,6-dihydroxy-7-nitro-benzo[b]thiophene-2-carbonyl)-amino]-benzoic acid, 3-chloro-5,6-dihydroxy-7-nitro-benzo[b]thiophene-2-carboxylic acid (4-methoxy-phenyl)amide, (3-chloro-5,6-dihydroxy-7-nitro-benzo[b]thiophen-2-yl)-(2,6-dimethyl-morpholin-4-yl)-methanone, (3-chloro-5,6-dihydroxy-7-nitro-benzo[b]thiophen-2-yl)-(4-hydroxy-piperidin-1-yl)-methanone, which are believed to be much more potent than entacapone and tolcapone due to their slower elimination via glucuronidation, For the purposes of this disclosure, the COMT inhibitors disclosed in WO 2007/010085 as well as BIA 9-1067 are considered to belong to a class of "highly potent COMT inhibitors." The predicted standard dose (the dose recommended to be used together with the above mentioned conventional proportion of levodopa to carbidopa) for a highly potent COMT inhibitor ranges from 0.1 mg to 50.

For the purposes of this disclosure, tolcapone and other such COMT inhibitors, the standard dose of which ranges from more than 50 mg to 200 mg, are considered to belong to a class of "moderately potent COMT inhibitors."

SUMMARY OF THE INVENTION

U.S. Provisional Patent Application No. 61/310,398 filed Mar. 4, 2010, is hereby incorporated by reference.

The present disclosure provides a method for the treatment of Parkinson's disease (PD) comprising simultaneously or sequentially administering to a patient in need of treatment of Parkinson's disease
(i) levodopa in an amount ranging from 50 mg to 300 mg,
(ii) carbidopa in an amount ranging from 25 mg to 150 mg or a therapeutically equivalent amount of another aromatic amino acid decarboxylase inhibitor, and
(iii) entacapone in an amount ranging from 50 mg to 300 mg, wherein the proportion of entacapone to carbidopa ranges from 0.33:1.0 to 3.2:1.0 by weight, a moderately potent COMT inhibitor in an amount ranging from 25 mg to 200 mg, wherein the proportion of said COMT inhibitor to carbidopa ranges from 0.16:1.0 to 3.08:1.0 by weight, or a highly potent COMT inhibitor in an amount ranging from 1 mg to 100 mg, wherein the proportion of said COMT inhibitor to carbidopa ranges from 0.006:1.0 to 1.54:1.0 by weight.

The present disclosure also provides a dosage form comprising
(i) levodopa in an amount ranging from 50 mg to 300 mg,
(ii) carbidopa in an amount ranging from 25 mg to 150 mg or a therapeutically equivalent amount of another aromatic amino acid decarboxylase Inhibitor, and
(iii) entacapone in an amount ranging from 50 mg to 300 mg, wherein the proportion of entacapone to carbidopa in said dosage form ranges from 0.33:1.0 to 3.2:1.0 by weight, a moderately potent COMT inhibitor in an amount ranging from 25 mg to 200 mg, wherein the proportion of said COMT inhibitor to carbidopa in said dosage form ranges from 0.16:1.0 to 3.08:1.0 by weight, or a highly potent COMT inhibitor in an amount ranging from 1 mg to 100 mg, wherein the proportion of said COMT inhibitor to carbidopa in said dosage form ranges from 0.006:1.0 to 1.54:1.0 by weight.

Patients that may benefit the most from the invention are those whose Parkinson's disease symptoms or motor complications such as on/off fluctuations have not been adequately controlled with their existing levodopa-AADC inhibitor therapy. Thus, a typical patient to be treated is an adult patient with Parkinson's disease having symptoms of end-of-dose wearing off.

DETAILED DESCRIPTION OF THE INVENTION

Figure 1:
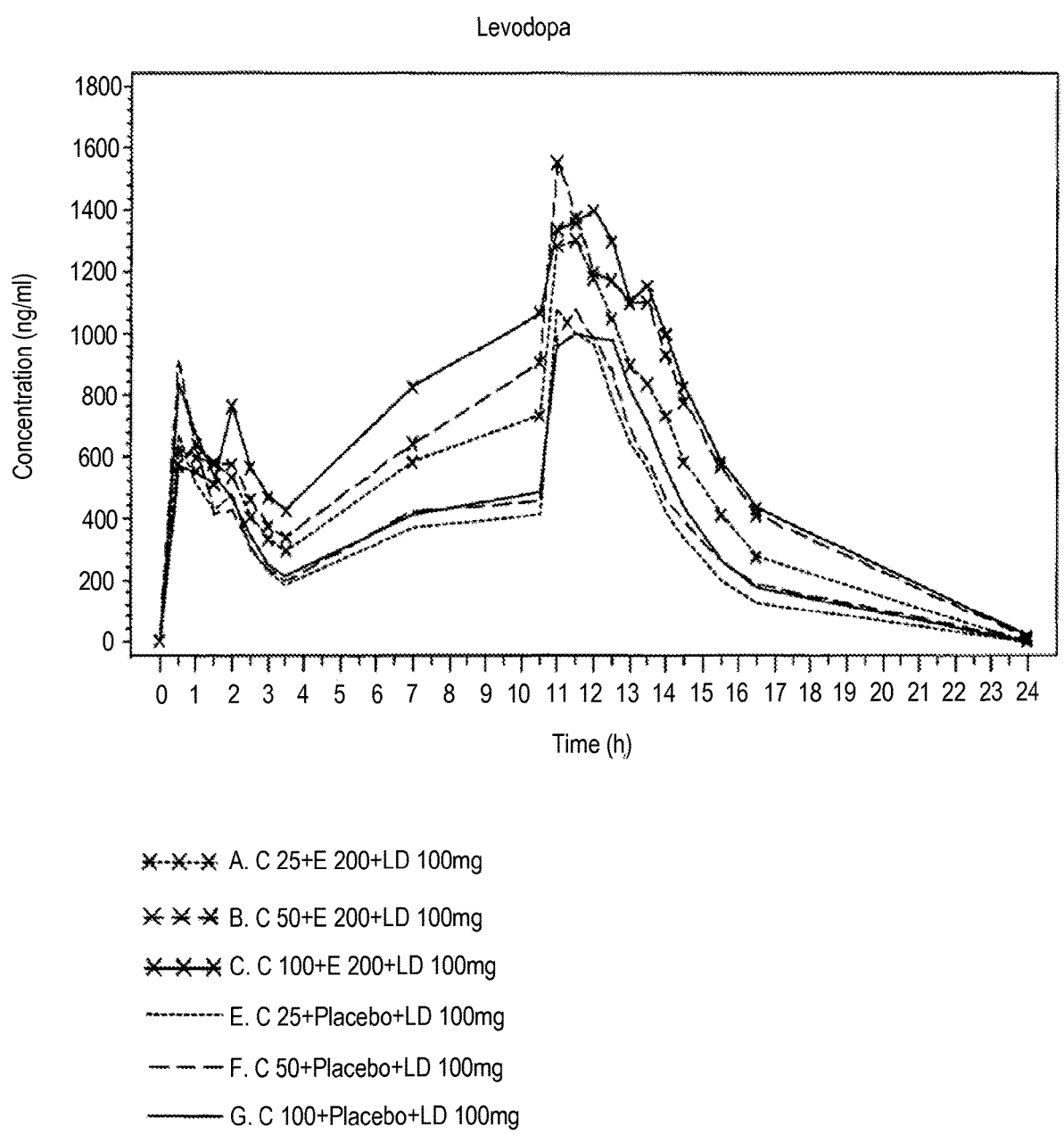
FIG. 1 shows the mean levodopa plasma concentrations (ng/ml) by study treatments:
A: Entacapone 200 mg+levodopa 100 mg+carbidopa 25 mg
B: Entacapone 200 mg+levodopa 100 mg+carbidopa 50 mg
C: Entacapone 200 mg+levodopa 100 mg+carbidopa 100 mg
E: Levodopa 100 mg+carbidopa 25 mg
F: Levodopa 100 mg+carbidopa 50 mg
G: Levodopa 100 mg+carbidopa 100 mg.

The most effective therapy for symptom control in Parkinson's Disease is levodopa therapy. However, with disease progression and long-term levodopa treatment, PD patients frequently experience motor complications, including wearing-off symptoms such as "end-of-dose wearing off" symptoms, "early morning dystonia" and "on/off fluctuations," and dyskinesia.

During end-of-dose wearing off, the effect of a dose of a PD drug decreases (wears off), the drug concentration decreases in plasma and subsequently in the brain, and the severity of PD symptoms, e.g., bradykinesia, rigidity, and resting tremor, are increased before the next dose is taken. Partly related to the motor symptoms and partly to the autonomic dysfunction, a PD patient with "end-of-dose wearing off" or "on/off fluctuations" may experience poor gastrointestinal tract mobility and swallowing difficulties.

In addition to the symptoms relating to motor function, the wearing-off symptoms may also include non-motor symptoms such as anxiety and pain. The reasons for the fluctuation episodes are not completely understood but may be, in part, related to oscillating plasma levels of levodopa in turn leading to intermittent or pulsatile stimulation of striatial dopamine receptors in the brain. End-of-dose wearing off symptoms or on/off fluctuations comprise alternations between periods of relatively good mobility ("on" periods) and periods of relatively impaired motor function ("off" periods) often associated with simultaneous non-motor symptoms. Dyskinesia are involuntary movements in the body of a PD patient often associated with high maximum or peak concentrations of a PD drug, such as levodopa. Thus, there is a continuing need to improve the present levodopa therapies by striving towards more steady plasma levels of levodopa and subsequently more continuous dopaminergic stimulation.

The inventors have surprisingly found that, in combination with a COMT inhibitor, AADC inhibition is not saturated by the currently used carbidopa dose, as with levodopa-carbidopa combination alone, but may be further enhanced by increased carbidopa doses, which may lead to improved levodopa pharmacokinetics and metabolism and subsequently may lead to improved control of PD symptoms and motor complications.

Unlike in traditional levodopa therapy, there may be no need to maintain a standard levodopa/carbidopa ratio (such as 4:1) across all dosage strengths, when using the treatment according to the invention. Furthermore, in combination with a COMT inhibitor, increased carbidopa doses may potentiate the pharmacodynamic effect on the AADC inhibition and subsequently may increase levodopa AUC throughout the dosing period despite the decreasing carbidopa plasma concentrations towards the end of said period. This is because by the increased carbidopa dose in the presence of a COMT inhibitor Cmin and AUC of levodopa are significantly increased. This means that, when a COMT inhibitor is given in conjunction with levodopa and an aromatic amino acid decarboxylase inhibitor, such as carbidopa, plasma levels of levodopa are higher and more sustained with the increased carbidopa dose than after administration of levodopa and an aromatic amino acid decarboxylase inhibitor alone.

It is believed that, at a given daily frequency of levodopa administration, those more sustained plasma levels of levodopa resulting from an increased carbidopa dose yield more constant dopaminergic stimulation in the brain, leading to improved control of the signs and symptoms of Parkinson's Disease, especially in end-of-dose wearing off and on/off fluctuations and in. As maximum concentrations of levodopa are not clinically significantly increased, the improved control of the signs and symptoms of Parkinson's Disease are not accompanied by increase of dopaminergic adverse effects or motor complications, such as dyskinesia, which would require reducing of the levodopa dose.

Furthermore, as the effect on levodopa is not sensitive to decreased plasma concentration of carbidopa towards the end of said period, no accumulation of carbidopa concentrations in plasma is seen. In fact, in the study, the concentrations were decreasing towards the end of the dosing period, which will reduce the probability of carbidopa passing the blood brain barrier and inhibiting AADC in the brain followed by subsequent increase of CNS side effects.

In combination with increased carbidopa dose, the COMT-inhibitor dose can also be reduced without significantly reducing AUC of levodopa. Reducing the amount of COMT-inhibitor would allow a smaller tablet size which would in turn benefit especially patients with swallowing difficulties. This would also be advantageous to reduce the risk of COMT inhibitor related gastrointestinal irritation and urine discoloration.

In combination with increased carbidopa dose, the COMT-inhibitor dose or potency can also be increased to an extent that will not significantly increase Cmax but win increase AUC of levodopa. Increasing the COMT-inhibitor potency would allow better control of PD symptoms. This would be advantageous to PD patients with wearing-off symptoms such as end-of-dose wearing off, early morning dystonia, and on/off fluctuations.

Thus, the present disclosure provides a method for the treatment of Parkinson's disease comprising simultaneously or sequentially administering to a patient in need of treatment of Parkinson's disease
(i) levodopa in an amount ranging from 50 mg to 300 mg,
(ii) carbidopa in an amount ranging from 25 mg to 150 mg or a therapeutically equivalent amount of another aromatic amino acid decarboxylase inhibitor, and
(iii) entacapone in an amount ranging from 50 mg to 300 mg, wherein the proportion of entacapone to carbidopa ranges from 0.33:1.0 to 3.2:1.0 by weight, a moderately potent COMT inhibitor in an amount ranging from 25 mg to 200 mg, wherein the proportion of said COMT inhibitor to carbidopa ranges from 0.16:1.0 to 3.08:1.0 by weight, or a highly potent COMT inhibitor in an amount ranging from 1 mg to 100 mg, wherein the proportion of said COMT inhibitor to carbidopa ranges from 0.006:1.0 to 1.54:1.0 by weight.

In one embodiment, the patient to be treated is an adult patient with Parkinson's disease experiencing symptoms of end-of-dose wearing off.

The present disclosure also provides a dosage form comprising
(i) levodopa in an amount ranging from 50 mg to 300 mg,
(ii) carbidopa in an amount ranging from 25 mg to 150 mg or a therapeutically equivalent amount of another aromatic amino acid decarboxylase inhibitor, and
(iii) entacapone in an amount ranging from 50 mg to 300 mg, wherein the proportion of entacapone to carbidopa in said dosage form ranges from 0.33:1.0 to 3.2:1.0 by weight, a moderately potent COMT inhibitor in an amount ranging from 25 mg to 200 mg, wherein the proportion of said COMT inhibitor to carbidopa in said dosage form ranges from 0.16:1.0 to 3.08:1.0 by weight, or a highly potent COMT inhibitor in an amount ranging from 1 mg to 100 mg, wherein the proportion of said COMT inhibitor to carbidopa in said dosage form ranges from 0.006:1.0 to 1.54:1.0 by weight.

The present disclosure also provides levodopa, an aromatic amino acid decarboxylase inhibitor, and entacapone for use in a method of treatment of Parkinson's disease by simultaneous or sequential administration to a patient of
(i) levodopa in an amount ranging from 50 mg to 300 mg,
(ii) carbidopa in an amount ranging from 25 mg to 150 mg or a therapeutically equivalent amount of another aromatic amino acid decarboxylase inhibitor, and
(iii) entacapone in an amount ranging from 50 mg to 300 mg, wherein the proportion of entacapone to carbidopa ranges from 0.33:1.0 to 3.2:1.0 by weight, a moderately potent COMT inhibitor in an amount ranging from 25 mg to 200 mg, wherein the proportion of said COMT inhibitor to carbidopa ranges from 0.16:1.0 to 3.08:1.0 by weight, or a highly potent COMT inhibitor in an amount ranging from 1 mg to 100 mg, wherein the proportion of said COMT inhibitor to carbidopa ranges from 0.006:1.0 to 1.54:1.0 by weight, optionally wherein carbidopa is replaced by a therapeutically equivalent amount of another aromatic amino acid decarboxylase inhibitor.

The present disclosure also provides use of levodopa, an aromatic amino acid decarboxylase inhibitor, and entacapone in the manufacture of a medicament for the treatment of Parkinson's disease by simultaneous or sequential administration to a patient of (i) levodopa in an amount ranging from 50 mg to 300 mg,
(ii) carbidopa in an amount ranging from 25 mg to 150 mg or a therapeutically equivalent amount of another aromatic amino acid decarboxylase inhibitor, and
(iii) entacapone in an amount ranging from 50 mg to 300 mg, wherein the proportion of entacapone to carbidopa ranges from 0.33:1.0 to 3.2:1.0 by weight, a moderately potent COMT inhibitor in an amount ranging from 25 mg to 200 mg, wherein the proportion of said COMT inhibitor to carbidopa ranges from 0.16:1.0 to 3.08:1.0 by weight, or a highly potent COMT inhibitor in an amount ranging from 1 mg to 100 mg, wherein the proportion of said COMT inhibitor to carbidopa ranges from 0.006:1.0 to 1.54:1.0 by weight, optionally wherein carbidopa is replaced by a therapeutically equivalent amount of another aromatic amino acid decarboxylase inhibitor.

The present disclosure also provides a dosage form comprising
(i) levodopa in an amount ranging from 50 mg to 300 mg,
(ii) carbidopa in an amount ranging from 25 mg to 150 mg or a therapeutically equivalent amount of another aromatic amino acid decarboxylase inhibitor, and
(iii) entacapone in an amount ranging from 50 mg to 300 mg, wherein the proportion of entacapone to carbidopa in said dosage form ranges from 0.33:1.0 to 3.2:1.0 by weight, a moderately potent COMT inhibitor in an amount ranging from 25 mg to 200 mg, wherein the proportion of said COMT inhibitor to carbidopa in said dosage form ranges from 0.16:1.0 to 3.08:1.0 by weight, or a highly potent COMT inhibitor in an amount ranging from 1 mg to 100 mg, wherein the proportion of said COMT inhibitor to carbidopa in said dosage form ranges from 0.006:1.0 to 1.54:1.0 by weight, for simultaneous or sequential use in the treatment of Parkinson's disease.

The present disclosure also provides a kit for simultaneous or sequential administration of levodopa, carbidopa or a therapeutically equivalent amount of another aromatic amino acid decarboxylase inhibitor, and entacapone, a moderately potent COMT inhibitor, or a highly potent COMT inhibitor, comprising:
(i) levodopa in an amount ranging from 50 mg to 300 mg;
(ii) carbidopa in an amount ranging from 25 mg to 150 mg or a therapeutically equivalent amount of another aromatic amino acid decarboxylase inhibitor; and
(iii) entacapone in an amount ranging from 50 mg to 300 mg, wherein the proportion of entacapone to carbidopa in said administration ranges from 0.33:1.0 to 3.2:1.0 by weight, a moderately potent COMT inhibitor in an amount ranging from 25 mg to 200 mg, wherein the proportion of said COMT inhibitor to carbidopa in said administration ranges from 0.16:1.0 to 3.08:1.0 by weight, or a highly potent COMT inhibitor in an amount ranging from 1 mg to 100 mg, wherein the proportion of said COMT inhibitor to carbidopa in said administration ranges from 0.006:1.0 to 1.54:1.0 by weight, wherein the kit may further comprise instructions for the simultaneous or sequential administration of the levodopa, carbidopa or a therapeutically equivalent amount of another aromatic amino acid decarboxylase inhibitor, and entacapone, a moderately potent COMT inhibitor, or a highly potent COMT inhibitor in the treatment of Parkinson's disease.

In one embodiment, levodopa is present in an amount ranging from 50 mg to 200 mg, carbidopa is present in an amount ranging from 65 mg to 125 mg, and entacapone is present in an amount ranging from 100 mg to 200 mg, wherein the proportion of entacapone to carbidopa ranges from 0.8:1.0 to 3.08:1.0 by weight.

In one embodiment, levodopa is present in an amount ranging from 75 mg to 175 mg, carbidopa is present in an amount ranging from 65 mg to 105 mg, and entacapone is present in an amount ranging from 100 mg to 200 mg, wherein the proportion of entacapone to carbidopa ranges from 0.95:1.0 to 3.08:1.0 by weight.

In one embodiment of the invention, levodopa is present in an amount ranging from 50 mg to 300 mg, for instance from 50 mg to 200 mg, such as from 75 mg to 125 mg, for example 50 mg, 75 mg, 100 mg, 125 mg, 150 mg, or 200 mg, for example 75 mg, 100 mg, 125 mg, 150 mg.

In one embodiment, carbidopa is present in an amount ranging from 65 mg to 150 mg, for instance from 65 mg to 125 mg, such as from 65 mg to 105 mg, for example 65 mg, 80 mg, 85 mg. 105 mg, or 125 mg.

In one embodiment, entacapone is present in an amount ranging from 50 mg to 300 mg, for instance from 50 mg to 200 mg, such as from 100 mg to 200 mg, for example 100 mg, 150 mg or 200 mg.

In one embodiment, the moderately potent COMT Inhibitor, such as tolcapone, is present in an amount ranging from 25 mg to 200 mg, for instance from 50 mg to 200 mg, such as from 50 mg to 100 mg, for example 50 mg, 100 mg, or 200 mg.

In one embodiment, the highly potent COMT inhibitor, such as BIA 9-1067, is present in an amount ranging from 1 mg to 100 mg, for instance from 1 mg to 50 mg, such as from 1 mg to 25 mg, for example 1 mg, 2.5 mg, 5 mg, 10 mg, or 25 mg.

In one embodiment, carbidopa is replaced by a therapeutically equivalent amount of another aromatic amino acid decarboxylase inhibitor, such as for instance with benserazide.

In one embodiment, the treatment and/or the dosage form is oral.

In one embodiment the treatment comprises administering orally a solid combination formulation.

In a further embodiment, the oral dosage form is an oral solid combination formulation In one embodiment, the proportion of entacapone to carbidopa ranges from 0.33:1.0 to 3.08:1.0 by weight, for instance from 0.8:1.0 to 2.35:1.0 by weight.

In one embodiment, the proportion of entacapone to carbidopa is 0.66:1.0, 0.80:1.0, 0.95:1.0, 1.18:1.0, 1.33:1.0, 1.54:1.0, 1.6:1.0, 1.9:1.0, 2.35:1.0, 2.5:1.0, or 3.08:1.0 by weight.

In one embodiment, the proportions of entacapone and carbidopa are 100 mg:125 mg, 100 mg:105 mg, 100 mg:85 mg, 100 mg:80 mg, 100 mg:65 mg, 200 mg:125 mg, 200 mg:105 mg, 200 mg:85 mg, 200 mg:80 mg, 200 mg:65 mg.

In one embodiment, the proportion of levodopa to carbidopa ranges from 0.4:1.0 to 3.1:1.0 by weight, for instance from 0.48:1.0 to 1.91:1.0 by weight.

In one embodiment, the proportions of levodopa and carbidopa are 50 mg:45 mg, 50 mg:65 mg, 50 mg:80 mg, 50 mg:85 mg, 50 mg:105 mg, 50 mg:125 mg, 75 mg:45 mg, 75 mg:65 mg, 75 mg:80 mg, 75 mg:85 mg, 75 mg:105 mg, 75 mg:125 mg, 100 mg:45 mg, 100 mg:65 mg, 100 mg:80 mg, 100 mg:85 mg, 100 mg:105 mg, 100 mg:125 mg, 125 mg:45 mg, 125 mg:65 mg, 125 mg:80 mg, 125 mg:85 mg, 125 mg:105 mg, 125 mg:125 mg, 150 mg:45 mg, 150 mg:65 mg, 150 mg:80 mg, 150 mg:85 mg, 150 mg:105 mg, 150 mg:125 mg, 200 mg:65 mg, 200 mg:80 mg, 200 mg:85 mg, 200 mg:105 mg, or 200 mg:125 mg.

In one embodiment, the proportions of levodopa, carbidopa and entacapone are 50 mg:65 mg:200 mg, 50 mg:80 mg:200 mg, 50 mg:85 mg:200 mg, 50 mg:105 mg:200 mg, 50 mg:125 mg:200 mg, 75 mg:65 mg:200 mg, 75 mg:80 mg:200 mg, 75 mg:85 mg:200 mg, 75 mg:105 mg:200 mg, 75 mg:125 mg:200 mg, 100 mg:65 mg:200 mg, 100 mg:80 mg:200 mg, 100 mg:85 mg:200 mg, 100 mg:105 mg:200 mg, 100 mg:125 mg:200 mg, 125 mg:65 mg:200 mg, 125 mg:80 mg:200 mg, 125 mg:85 mg:200 mg, 125 mg:105 mg:200 mg, 125 mg:125 mg:200 mg, 150 mg:65 mg:200 mg, 150 mg:80 mg:200 mg, 150 mg:85 mg:200 mg, 150 mg:105 mg:200 mg, 150 mg:125 mg:200 mg, 100 mg, 200 mg:65 mg:200 mg, 200 mg:80 mg:200 mg, 200 mg:85 mg:200 mg, 200 mg:105 mg:200 mg, or 200 mg:125 mg:200 mg.

In one embodiment, the proportions of levodopa, carbidopa and entacapone are 50 mg:65 mg:200 mg, 50 mg:80 mg:200 mg, 50 mg:85 mg:200 mg, 50 mg:105 mg:200 mg, 75 mg:65 mg:200 mg, 75 mg:80 mg:200 mg, 75 mg:85 mg:200 mg, 75 mg:105 mg:200 mg, 100 mg:65 mg:200 mg, 100 mg:80 mg:200 mg, 100 mg:85 mg:200 mg, 100 mg:105 mg:200 mg, 125 mg:65 mg:200 mg, 125 mg:80 mg:200 mg, 125 mg:85 mg:200 mg, 125 mg:105 mg:200 mg, 150 mg:65 mg:200 mg, 150 mg:80 mg:200 mg, 150 mg:85 mg:200 mg, 150 mg:105 mg:200 mg, 200 mg:65 mg:200 mg, 200 mg:80 mg:200 mg, 200 mg:85 mg:200 mg, or 200 mg:105 mg:200 mg.

In one embodiment, the proportions of levodopa, carbidopa and entacapone are 75 mg:65 mg:200 mg, 75 mg:85 mg:200 mg, 75 mg:105 mg:200 mg, 100 mg:65 mg:200 mg, 100 mg:85 mg:200 mg, 100 mg:105 mg:200 mg, 125 mg:65 mg:200 mg, 125 mg:85 mg:200 mg, 125 mg:105 mg:200 mg, 150 mg:65 mg:200 mg, 150 mg:85 mg:200 mg, or 150 mg:105 mg:200 mg.

In one embodiment of the invention, the daily dose of levodopa ranges from 150 mg to 1500 mg, for instance from 300 mg to 1250 mg, such as from 300 mg to 900 mg, wherein the total number of daily doses ranges from 3 to 10, for instance from 3 to 7, such as from 4 to 6, such as 4 or 5 or 6.

In one embodiment of the invention, the daily dose of carbidopa ranges from 135 mg to 1250 mg, for instance from 195 mg to 1050 mg, such as form 255 mg to 850 mg, wherein the total number of daily doses ranges from 3 to 10, for instance from 3 to 7, such as from 4 to 6, such as 4 or 5 or 6.

In one embodiment of the invention the highly potent COMT inhibitor is BIA 9-1067 (5-[3-(2,5-dichloro-4,6-dimethyl-1-oxypyridin-3-yl)-[1,2,4]oxadiazol-5-yl]-3-nitrobenzene-1,2-diol) In one embodiment the daily dose of BIA 9-1067 is 25 mg or 50 mg given once-a-day. BIA 9-1067 is a poorly soluble drug. WO 2009/108077 discloses a solid dosage form for the release of a poorly soluble active pharmaceutical ingredient such as BIA 9-1067.

In one embodiment the proportion of BIA 9-1067 to carbidopa ranges from 0.01:1.0 to 0.16:1.0 by weight, for instance from 0.02:1.0 to 0.1:1.0 by weight.

In one embodiment the proportions of BIA 9-1067 and carbidopa are 2.5 mg:65 mg, 2.5 mg:85 mg, 2.5 mg:105 mg, 5.0 mg:65 mg, 5.0 mg:85 mg, 5.0 mg:105 mg, 10.0 mg:65 mg, 10.0 mg:85 mg or 10.0 mg:105 mg.

In one embodiment the proportions of levodopa, carbidopa and BIA 9-1067 are 75 mg:65 mg:2.5 mg, 75 mg:85 mg:2.5 mg, 75 mg:105:2.5 mg, 100 mg:65 mg:2.5 mg, 100 mg:85 mg:2.5 mg, 100 mg:105 mg:2.5 mg, 125 mg:65 mg:2.5 mg, 125 mg:85 mg:2.5 mg, 125 mg:105 mg:2.5 mg, 150 mg:65 mg:2.5 mg, 150 mg:85 mg:2.5 mg, 150 mg:105 mg:2.5 mg, 75 mg:65 mg:5.0 mg, 75 mg:85 mg:5.0 mg, 75 mg:105:5.0 mg, 100 mg:65 mg:5.0 mg, 100 mg:85 mg: 5.0 mg, 100 mg:105 mg:5.0 mg, 125 mg:65 mg:5.0 mg, 125 mg:85 mg:5.0 mg, 125 mg:105 mg:5.0 mg, 150 mg:65 mg:5.0 mg, 150 mg:85 mg:5.0 mg, 150 mg:105 mg:5.0 mg, 75 mg:65 mg:10.0 mg, 75 mg:85 mg:10.0 mg, 75 mg:105: 10.0 mg, 100 mg:65 mg:10.0 mg, 100 mg:85 mg: 10.0 mg, 100 mg:105 mg:10.0 mg, 125 mg:65 mg:10.0 mg, 125 mg:85 mg:10.0 mg, 125 mg:105 mg:10.0 mg, 150 mg:65 mg:10.0 mg, 150 mg:85 mg:10.0 mg, 150 mg:105 mg:10.0 mg.

In one embodiment of the invention, the daily dose of entacapone ranges from 150 mg to 2000 mg, for instance from 300 mg to 2000 mg, such as from 300 mg to 1600 mg, wherein the total number of daily doses ranges from 3 to 10, for instance from 3 to 8, such as from 4 to 6, such as 4 or 5 or 6. In one embodiment of the invention, the daily dose of tolcapone or another moderately potent COMT inhibitor ranges from 75 mg to 1200 mg, for instance from 150 mg to 800 mg, such as from 300 mg to 600 mg, wherein the total number of daily doses ranges from 3 to 10, for instance from 3 to 7, such as from 3 to 5, such as 3 or 4 or 5. In one embodiment of the invention, the daily dose of a highly potent COMT inhibitor ranges from 1 mg to 500 mg, for instance from 5 mg to 100 mg, such as from 10 mg to 100 mg, wherein the total number of daily doses ranges from 1 to 10, for instance from 1 to 7, such as from 1 to 3, such as 1 or 2 or 3.

It is to be understood that whenever a given amount of levodopa, carbidopa, benserazide, or other AADC inhibitor or entacapone or other COMT inhibitor is mentioned herein in the context of this disclosure it is meant to comprise also an equivalent amount of a pharmaceutically acceptable salt, prodrug (including ester) or hydrate.

It is also to be understood that the amounts and ranges mentioned in this disclosure apply to all embodiments disclosed herein whether methods (i.e. methods for the treatment or methods for the manufacture) or dosage forms.

Definitions

The term "treatment of Parkinson's Disease" refers to relieving and/or delaying of the worsening of one of more of the symptoms and/or motor complications related to idiopathic Parkinson's Disease, e.g. bradykinesia, rigidity, and resting tremor.

The term "adult patient" means a patient 18 years of age or older.

The term "symptoms of end-of-dose wearing-off" refers to the shortening of the duration of the motor response after a PD drug intake and increasing the severity of e.g. bradykinesia, rigidity, and resting tremor. The term comprises the so-called predictable end-of-dose motor fluctuations characterised by end-of-dose failure of the symptom control. End-of-dose wearing-off symptoms may also include fluctuating non-motor symptoms, such as anxiety and pain. Motor complications may also include rapid and unpredictable swings from mobility to immobility ("on-off" phenomenon).

The term "simultaneous" or "simultaneously" refers to administration of the disclosed drug substances at the same time in separate formulations or as a combination formulation, i.e. in a single dosage form.

The term "sequential" or "sequentially" refers to administration of the disclosed drug substances one after the other. i.e., not at the same time, in two or more separate dosage forms, for example entacapone may be administered as a separate dosage form and levodopa and carbidopa may be administered in a combination formulation, or carbidopa may be administered, followed by levodopa, then by entacapone. If the disclosed drug substances are administered sequentially, then typically administration of the last drug substance is begun an hour or less, generally 30 minutes or less, after administration of the first drug substance is begun.

The term "oral solid dosage form" refers to a single or multi-unit solid oral dosage form. A single oral dosage form may be a combination formulation, such as a tablet, which comprises two or more of the drug substances. In one embodiment the single oral dosage form is a combination formulation, such as a tablet, which comprises all of the drug substances. A multi-unit solid oral dosage form may be a dosage form comprising a plurality of oral solid units in the form of small particles (for instance a capsule or sachet filled with minitablets, granules or pellets) which, when taken simultaneously or sequentially, provide a unit dose. The terms "multiple-unit" or "multi-particulate" oral dosage form may also be used to refer to such a multi-unit solid oral dosage form. The particles may be also be used as such in a so-called sprinkle form that can be sprinkled directly onto food or liquids for easy ingestion. Multiple-unit dosage forms have been accepted to provide advantages over single unit dosage forms. The pharmacokinetics of the drug release from a multiple unit dosage form is more uniform than from the single unit dosage form, because the pharmacokinetics of the drug release from a multiple unit dosage form is the average value of the kinetics of the drug release from individual subunits. The units of a multiple unit dosage form may scatter freely in the gastrointestinal tract and act like liquids, leaving the stomach within a short period of time, which results in improved biopharmaceutical characteristics, such as improved bioavailability, reduced food effect on plasma profiles and ultimately reduced variability of plasma profiles and a lower possibility of local irritation in gastrointestinal tract. In addition, a multi-unit solid oral dosage form may be individual tablets that contain the drug substances. For example, a multi-unit solid oral dosage form can include entacapone in one tablet and a separate tablet containing levodopa and carbidopa.

The terms "repeated dose" and "in a repeated manner" refers to multiple administration of a drug during a day, usually from at least 3 up to 10 times a day depending on the severity of the disease of a patient with Parkinson's Disease and on the subsequent need of levodopa. For instance, levodopa is usually administered in a repeated manner and simultaneously or sequentially with an AADC inhibitor. However, a highly potent COMT inhibitor may be administered in combination with repeated dose levodopa and AADC inhibitor only once a day or even less frequently and a moderately potent COMT inhibitor may be administered one to three times per day.

The "standard dose" may be used to determine whether a COMT inhibitor may be considered to be a highly potent inhibitor or a moderately potent inhibitor. As potency increases, less inhibitor is required to reach 80% inhibition of soluble COMT in human erythrocytes (Shultz, E. and Nissinen, E., Biomedical Chromatography, Vol. 3, No. 2, 1989, 64-67 and Nohta. H. et al, Journal of Chromatography, 308 (1984) 93-100). For example, a moderately potent COMT inhibitor will require more than 200 mg in a single dose to reach 80% inhibition, typically from more than 200 mg to 800 mg in a single dose. A highly potent inhibitor will need 200 mg or less in a single dose to reach 80% inhibition. A more potent inhibitor will also provide effective inhibition for a longer period of time. Thus, a moderately potent inhibitor when administered in a 200 mg dose will maintain 40% or more effective inhibition of soluble COMT in human erythrocytes for from 2 hours to less than 8 hours, typically from 3 to 6 hours. A highly potent inhibitor when administered in a dose of 100 mg will maintain 40% or more effective inhibition of soluble COMT in human erythrocytes for 8 hours or more. Suitable conditions for measuring effective inhibition of soluble COMT in human erythrocytes are described in Keränen, T. et al, Eur. J. Clin. Pharmcol (1994) 46:151-157 and Dingemanse, J. et al, Clinical Pharmacology & Therapeutics, May 1995, 508-517).

The term "pharmaceutically acceptable salt" refers to a salt of a compound that is pharmaceutically acceptable and that possesses the desired pharmacological activity of the parent compound. Representative examples of pharmaceutically acceptable salts include, but are not limited to, acid addition salts with inorganic or organic acids, for instance, chlorides, bromides, sulfates, nitrates, phosphates, sulfonates, methane sulfonates, formates, tartrates, maleates, citrates, benzoates, salicylates, ascorbates, acetates, and oxalates. The pharmaceutically acceptable form can be in the form of an anhydrate or a hydrate.

The term "prodrug" refers to a derivative of a drug substance which releases said active parent drug substance in vivo when such prodrug is administered to a patient. There are several publications disclosing different prodrugs of levodopa, for instance, levodopa methyl ester has been under development by Chiesi under trademark LEVOMET®, an ethylester has been disclosed in U.S. Pat. No. 5,607,969 and more complex esters have been disclosed in EP 0 309 827 B, WO 2005/121069 and WO 2007/067495. Also, various carbidopa prodrugs have been disclosed e.g. in GB 940,596 and WO 2004/052841.

The term "ester" refers to an ester of a compound that is pharmaceutically acceptable and that possesses the desired pharmacological activity of the parent compound. Such esters may be prepared by known methods using pharmaceutically acceptable acids that are conventional in the field of pharmaceuticals. Non-limiting examples of these esters include esters of aliphatic or aromatic alcohols. Representative examples of pharmaceutically acceptable esters include, but are not limited to, methyl, ethyl, n-propyl, iso-propyl, n-butyl, iso-butyl, sec-butyl, tort-butyl, and benzyl esters. There are several publications disclosing different esters of levodopa, for instance, several levodopa esters have been disclosed in EP 309 827, an ethyl ester has been disclosed in U.S. Pat. No. 5,607,969 and the methyl ester has been under development by Chiesi under trademark LEVOMET®. Also various carbidopa esters have been disclosed e.g. in GB 940,596. The pharmaceutically acceptable form can be in the form of an anhydrate or hydrate.

The term "a therapeutically equivalent amount" as used herein refers to an amount of an aromatic amino acid decarboxylase inhibitor other than carbidopa that is capable of causing a similar therapeutic response as the dose of carbidopa, when used according to the present disclosure. For example, 50 mg of benserazide hydrochloride is considered to be capable of causing a similar therapeutic response as 50 mg of carbidopa, when used according to the present disclosure.

The terms "substantially separated" and "substantial separation" refer to that a considerable or ample amount of said drug substance is kept apart from the other drug substance(s), for example, that a considerable amount of carbidopa is kept apart from entacapone. There may be several ways to accomplish said separation, for example, by granulating all or at least one of the drug substances separately. No specific separation layer is needed to cause said substantial separation. It is also to be noted that even though all drug substances would be granulated separately, there will always be small amounts of said drug substance as a powder. In one embodiment, before granulating and incorporating a drug substance in a single dosage unit with other drug substances, they may undergo pre-processing in a manner indicated below.

The term "substantial portion" refers to that at least 80% of said drug substance is handled using the technology in question. For instance, granulating a substantial portion of carbidopa means that from 80% to 100% is granulated. If 90% is granulated, then 10% is added as such. The term "granule" refers to a pharmaceutical formulation whereby the ingredients have been mixed together in order to intimately and evenly disperse the drug substance(s) within some or all of the other ingredients and to increase the particle size. Well known techniques are known in the pharmaceutical industry and can be selected from wet, melt granulation or dry granulation.

The terms "granulating" and "granulation" refer to methods, wherein one or more drug substances are brought into contact with at least one pharmaceutically acceptable excipient and granulated. The granulation method may be any granulation method known in the art such as dry granulation, melt granulation or wet granulation or the like. All unit operations typically needed to perform granulation, such as sieving and drying are meant to be included in said granulation step in the context of this disclosure. Furthermore, it is possible to coat the granules made according to the invention, for instance, when they are intended to be administered to the patient as such. Suitable granulation methods have been described, for instance in the book: The Theory and Practice of Industrial Pharmacy $3^{rd}$ edition, Lachman L, Lieberman H A and Kanig J L, Lea & Febiger, Philadelphia, 1986 and the Handbook of Pharmaceutical Excipients $5^{th}$ edition, edited by Rowe R C, Sheskey P J and Owen S C, Pharmaceutical Press, 2006. The details of the pharmaceutically acceptable excipients used therein have been described, for instance in Pharmaceutics, The Science of Dosage Form Design, $2^{nd}$ edition. Aulton M E, Churchill Livingstone, 2002. Suitable melt granulation technologies have been described, for instance, in Handbook of Pharmaceutical Granulation Technology, Ed. by Dilip M. Parikh, Marcel Dekker, Inc. New York, $2^{nd}$ print, 1997. The drug substances to be used in the granulation method may be pre-processed before the granulation. Pre-processing may also generally be applied to drug substances before formulating into a dosage form without granulation. For example, a drug substance in the form of a powder may be pre-processed before formulation into a dosage form.

The terms "pre-processed" and "pre-processing" refer to pre-treatment of each of the drug substances, either individually or together with another drug substance, before further processing, such as before granulation or before formulating a powder into a dosage form. Suitable pre-processing methods can be, for example, sieving, de-dusting, gas treatment, conditioning, milling and optionally mixing, de-aggregation, de-agglomeration or treatment with pharmaceutically acceptable excipients, for example, with glidants such as colloidal silicon dioxide.

The term "mixing" and "preparing a mixture" refer to the meaning used in the art of manufacturing pharmaceutical dosage forms Suitable mixing technologies have been described, for example in the above mentioned handbooks.

The term "bilayered tablet" refers to a tablet, wherein there are two layers horizontally on the top of each other or there is an inner core comprising either one or two of the drug substances and an outer layer comprising at least one drug substance. For example, there may be an outer layer comprising carbidopa and levodopa or carbidopa alone and an inner core comprising entacapone and levodopa or entacapone alone. It is also possible to divide one or more drug substances between two layers, for instance, carbidopa may be divided between the outer layer and the inner core. This type of tablets and the preparation thereof have been described, for instance, in WO 2008/053297. Other suitable technologies have been described, for instance in the book: The Theory and Practice of Industrial Pharmacy $3^{nd}$ edition. Lachman L, Lieberman H A and Kanig J L, Lea & Febiger, Philadelphia, 1986. It is to be noted that there may be always one or more Inert layers (e.g. layers prepared without separately adding a drug substance) in such a bilayered tablet. Likewise, it is possible that there is an inert inner core, for instance, a non-pareil inside the tablet.

The terms "trilayered tablet" and "multilayered" tablets refer to tablets, wherein there are three or more layers horizontally on the top of each other or there is an inner core or layer comprising one of the drug substances a second layer comprising another drug substance and a third layer comprising the third drug substance. For example, there may be an outer layer comprising carbidopa and the next layer comprising levodopa and an inner core or layer comprising entacapone. It is also possible to divide one or more drug substance into several layers, for instance, carbidopa may be divided between the outer layer and the second layer. Other suitable technologies have been described, for instance in the book: Pharmaceutical Dosage Forms and Drug Delivery Systems, $7^{th}$ edition, Ansell H C, Allen L V and Popovich N G, Lippincott Williams & Wilkins, 1999. It is to be noted that there may be always one or more inert layers (e.g. layers prepared without separately adding a drug substance) in such a trilayered or multilayered tablet. Likewise, it is possible that there is an inert inner core, for instance, a non-pareil inside the tablet.

The term "minitablet" refers to a compressed pharmaceutical formulation that has dimensions of length and breadth (or, depending on its shape, a diameter) each equal to or less than 5 mm.

The term "pellet" refers to a substantially spherical solid particle whose diameter size may range from about 100 microns to about 3 mm that has been made by layering onto a particle (for instance, on a non-pareil) or extrusion optionally followed by spheronisation or other similar known techniques. Generally pellets are more spherical in appearance than mini-tablets.

The term "immediate release" refers to a pharmaceutical dosage form which releases levodopa immediately upon administration and will result in 80-100%, preferably 90-100% dissolution of the dose amount within one hour. Dissolution method: USP apparatus I: 50 rpm; medium: 0.1 N hydrochloric acid, 750 ml.

The pharmaceutical dosage forms of the present invention can be present in the form of monolayered or multilayered (for instance, bilayered or trilayered tablets), minitablets, capsules, granules, pellets, or minitablets, granules, pellets or a combination of the same in a capsule or the like.

There are several different ways to prepare the dosage form(s) according to the invention. In discussing the preparation of the dosage forms we will, for simplicity, refer to the COMT inhibitor as entacapone. However it should be understood that the methods described here for entacapone are equally suitable for use with another COMT inhibitor in which the amount of the COMT inhibitor is adjusted as appropriate and as would be evident to the skilled person on the basis of the standard dose for the COMT inhibitor. Similarly, for simplicity the aromatic amino acid decarboxylase inhibitor is referred to as carbidopa, but it should be understood that the methods described are equally suitable for use with another AADC inhibitor in which the amount of AADC inhibitor is adjusted as appropriate.

One way to prepare a dosage form according to the invention is to first formulate carbidopa substantially separately from entacapone and levodopa before formulating into the dosage form, for example, in the manner disclosed in U.S. Pat. No. 6,500,867 describing fixed oral combinations of entacapone, levodopa and carbidopa, wherein carbidopa is substantially separated from entacapone and levodopa. Another way is to first formulate entacapone substantially separately from levodopa and carbidopa before formulating into the dosage form. One particular such way is to use separate entacapone-containing granules or granule mixtures, for example using the technologies disclosed in WO 2006/131591, and combine said granules or granule mixtures with levodopa and AADC inhibitor either in a fixed combination formulation or as two separate dosage forms. A further way of preparing dosage forms according to the invention is to first formulate part of the levodopa content with entacapone and a further part of the levodopa content with carbidopa, before formulating into the dosage form optionally together with a further part of the levodopa content added as such. A yet further way is to prepare a mixture of levodopa, carbidopa and entacapone, of which any part may optionally be pre-processed, before formulating into the dosage form.

Thus, in one embodiment of the invention entacapone and carbidopa are substantially separated from each other. There are several different techniques to accomplish said separation. It can be made, for instance, by granulating levodopa and entacapone together or separately and adding carbidopa as such (i.e. non-granulated carbidopa, for example, in powder form) and/or as granules; or by granulating levodopa and carbidopa and adding entacapone as such (i.e. non-granulated entacapone, for example, in powder form) or in the form of granules. Any known granulation method, for example, wet granulation, melt granulation and dry granulation can be used, but preferably the granulation method is wet granulation. Suitable granulation methods are known in the art and suitable excipients are listed in, for instance in WO 2006/131591.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating substantial portion of entacapone and substantial portion of levodopa either together or separately
(b) optionally granulating all or any portion of carbidopa
(c) combining the product obtained in step (a) with the product of step (b) or carbidopa as such or a mixture thereof; and
(d) formulating the product obtained in step (c) as well as the rest of entacapone and/or levodopa, if any, into tablets or minitablets or filling the same directly into capsules, sachets or a dispenser. This method is preferred, when flexibility in the release properties of the drug substances is required.

In a particular embodiment of the invention a method for the preparation of a oral solid dosage form comprising (i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating entacapone and levodopa either together or separately
(b) granulating carbidopa
(c) combining the product obtained in step (a) with the product of step (b); and
(d) formulating the product obtained in step (c) into tablets or minitablets.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating entacapone and levodopa either together or separately
(b) granulating from 5 to 80% of carbidopa
(c) combining the product obtained in step (a) with the product of step (b) and the rest of carbidopa as such; and
(d) formulating the product obtained in step (c) into tablets or minitablets or filling the same directly into capsules, sachets or a dispenser.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating entacapone and levodopa either together or separately
(b) granulating from 5 to 40% of carbidopa
(c) combining the product obtained in step (a) with the product of step (b) and the rest carbidopa as such; and
(d) formulating the product obtained in step (c) into tablets or minitablets or filling the same directly into capsules, sachets or a dispenser.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating entacapone and levodopa either together or separately
(b) granulating from 15 to 20% of carbidopa
(c) combining the product obtained in step (a) with the product of step (b) and the rest carbidopa as such; and
(d) formulating the product obtained in step (c) into tablets or minitablets or filling the same directly into capsules, sachets or a dispenser.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating entacapone and levodopa either together or separately
(b) combining the product obtained in step (a) with carbidopa as such; and
(c) formulating the product obtained in step (c) into tablets.
This method provides a simple manufacturing process and a good stability for the product.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) formulating a substantial portion of entacapone and a substantial portion of levodopa either together or independently into granules, minitablets or pellets
(b) formulating a substantial portion of carbidopa into granules, minitablets or pellets; and
(c) combining the product obtained in step (a) with the product of step (b) and the rest of the drug substances if any, and filling it into capsules, sachets or a dispenser.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) formulating a substantial portion of entacapone and a substantial portion of levodopa either together or independently into granules, minitablets or pellets
(b) formulating a substantial portion of carbidopa into granules, minitablets or pellets; and
(c) formulating the product obtained in step (a) and product of step (b) and the rest of the drug substances, if any, into a monolayered, bilayered, threelayered or a multilayered tablet.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising (a) granulating substantial portion of levodopa and substantial portion of carbidopa either together or separately
(b) optionally granulating all or any portion of entacapone
(c) combining the product obtained in step a) with the product obtained in step (b), or entacapone as such or a mixture thereof; and
(d) formulating the product obtained in step (c) an the rest of levodopa and/or carbidopa, if any, into tablets or minitablets or filling the same directly into capsules, sachets or a dispenser. Preferably, levodopa and carbidopa are granulated together.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.686:1.0 to 3.08:1.0 by weight, is provided comprising
(a) granulating levodopa and carbidopa either together or separately
(b) granulating entacapone
(c) combining the product obtained in step a) with the product obtained in step (b); and
(d) formulating the product obtained in step (c) into tablets or minitablets or filling it or said minitablets into capsules, sachets or a dispenser. Preferably, levodopa and carbidopa are granulated together.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating levodopa and carbidopa either together or separately
(b) granulating from 5 to 100% of entacapone
(c) combining the product obtained in step a) with the product obtained in step (b); and the rest of entacapone as such; and
(d) formulating the product obtained in step (c) into tablets or minitablets or filling the same directly into capsules, sachets or a dispenser.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating levodopa and carbidopa either together or separately
(b) granulating from 10 to 75% of entacapone
(c) combining the product obtained in step a) with the product obtained in step (b); and the rest of entacapone as such; and
(d) formulating the product obtained in step (c) into tablets or minitablets or filling the same directly into capsules, sachets or a dispenser.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating levodopa and carbidopa either together or separately
(b) granulating from 15 to 50% of entacapone
(c) combining the product obtained in step a) with the product obtained in step (b); and the rest of entacapone as such; and
(d) formulating the product obtained in step (c) into tablets or minitablets or filling the same directly into capsules, sachets or a dispenser.

In a particular embodiment of the invention a method for the preparation of a oral solid dosage form comprising
(i) levodopa in an amount ranging from 50 mg to 200 mg.
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) granulating levodopa and carbidopa either together or separately
(b) combining the product obtained in step (a) with entacapone as such; and
(c) formulating the product obtained in step (b) into tablets or minitablets.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is
(a) formulating carbidopa and levodopa either together or independently into granules, minitablets or pellets
(b) formulating entacapone into granules, minitablets or pellets; and filling the products obtained in steps (a) and (b) into capsules, sachets or a dispenser. Preferably, levodopa and carbidopa are formulated together.

Yet another suitable way of separating entacapone and carbidopa has been described in WO 2010/108845 disclosing a dosage form comprising a) a first mixture of 10 to 75% by weight of the total amount of levodopa with all entacapone present in the composition and b) a second mixture of 25 to 90% by weight of total levodopa with all carbidopa present in the composition and c) optionally, a third mixture comprising the remaining levodopa, if any. To accomplish the separation of carbidopa and entacapone, the two mixtures a) and b) are prepared such that they are not both in powder form. The same principles, manufacturing processes and excipients as disclosed in WO 2010/108845 may be used to prepare the dosage form also according to the present invention.

Thus, in one embodiment of the invention a method for the preparation of a oral solid dosage form comprising
(i) levodopa in an amount ranging from 50 mg to 200 mg.
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
a) preparing a first mixture of 10 to 75% by weight of the total amount of levodopa with all entacapone present in the composition,
b) preparing a second mixture of 25 to 90% by weight of total levodopa with all carbidopa present in the composition; and
c) optionally preparing a third mixture comprising the remaining levodopa; and
d) formulating the products obtained in steps (a) and (b) and optionally (c) independently into granules, tablets, minitablets or pellets and optionally filling the said granules, minitablets or pellets into capsules, sachets or a dispenser. Preferably, when the products of step (a) and (b) are formulated together, then (a) and (b) are not both in powder form.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
a) granulating from 10 to 75% by weight of the total amount of levodopa with all entacapone present in the composition,
b) granulating from 25 to 90% by weight of total levodopa with all carbidopa present in the composition; and
c) optionally preparing a third mixture comprising the remaining levodopa; and
d) formulating the products obtained in steps (a) and (b) and (c) if any into tablets or minitablets and optionally filling the said granules or minitablets into capsules, sachets or a dispenser.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
a) preparing a first mixture of 30 to 90% by weight of the total amount of levodopa with all entacapone present in the composition,
b) preparing a second mixture of 10 to 70% by weight of total levodopa with all carbidopa present in the composition; and
c) optionally preparing a third mixture comprising the remaining levodopa; and
d) formulating the products obtained in steps (a) and (b) and optionally (c) independently into granules, tablets, minitablets or pellets and optionally filling the said granules, minitablets or pellets into capsules, sachets or a dispenser. Preferably, when the products of step (a) and (b) are formulated together, then product (a) and (b) are not both in powder form.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
a) preparing a first mixture of 50 to 80% by weight of the total amount of levodopa with all entacapone present in the composition,
b) preparing a second mixture of 20 to 50% by weight of total levodopa with all carbidopa present in the composition; and
c) optionally preparing a third mixture comprising the remaining levodopa; and
d) formulating the products obtained in steps (a) and (b) and optionally (c) independently into granules, tablets, minitablets or pellets and optionally filling the said granules, minitablets or pellets into capsules, sachets or a dispenser. Preferably, when the products of step (a) and (b) are formulated together, then product (a) and (b) are not both in powder form.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
a) granulating 30 to 90% by weight of the total amount of levodopa with all entacapone present in the composition,
b) granulating of 10 to 70% by weight of total levodopa with all carbidopa present in the composition; and
c) optionally preparing a third mixture comprising the remaining levodopa; and
d) formulating the products obtained in steps (a) and (b) and (c) if any, into tablets or minitablets and optionally filling the said granules or minitablets into capsules, sachets or a dispenser.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
a) granulating 50 to 80% by weight of the total amount of levodopa with all entacapone present in the composition,
b) granulating of 20 to 50% by weight of total levodopa with all carbidopa present in the composition; and
c) optionally preparing a third mixture comprising the remaining levodopa; and d) formulating the products obtained in steps (a) and (b) and (c) if any, into tablets or minitablets and optionally filling the said granules or minitablets into capsules, sachets or a dispenser.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) preparing a mixture of optionally pre-processed levodopa, optionally pre-processed carbidopa and optionally pre-processed entacapone,
(b) formulating the product obtained in step (a) into granules, tablets, minitablets, pellets and optionally filling said granules, minitablets or pellets into a capsule, sachet or a dispenser.

In a particular embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided comprising
(a) preparing a mixture of optionally pre-processed levodopa, optionally pre-processed carbidopa and optionally pre-processed entacapone,
(b) compressing the product obtained in step (a) into tablets. This method provides a simple and robust manufacturing process, wherein also non-micronized drug substances (for instance, medium sized or coarse entacapone) may be used.

In one embodiment of the invention an oral solid dosage form is provided comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, allowing 80-100% of levodopa to be released within one hour in a dissolution test (USP apparatus I (baskets) 50 rpm, medium: 0.1 N hydrochloric acid, volume 750 ml) from said dosage form.

In one embodiment of the invention an oral solid dosage form is provided comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, allowing from 90 to 100% of levodopa to be released within one hour in a dissolution test (USP apparatus I (baskets) 50 rpm, medium: 0.1 N hydrochloric acid, volume 750 ml) from said dosage form.

In one embodiment of the invention an oral solid dosage form is provided comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, allowing from 20 to 100% of carbidopa to be released within one hour in a dissolution test (USP apparatus I (baskets) 50 rpm, medium: 0.1 N hydrochloric acid, volume 750 ml) from said dosage form.

In one embodiment of the invention an oral solid dosage form is provided comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, allowing from 40 to 100% of carbidopa to be released within one hour in a dissolution test (USP apparatus I (baskets) 50 rpm, medium: 0.1 N hydrochloric acid, volume 750 ml) from said dosage form.

In one embodiment of the invention an oral solid dosage form is provided comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, allowing from 20 to 100% of entacapone to be released within 60 minutes in a dissolution test (USP apparatus I (baskets) 125 rpm, medium: phosphate buffer pH 5.5, volume 900 ml) from said dosage form.

In one embodiment of the invention an oral solid dosage form is provided comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, allowing from 40 to 100% of entacapone to be released within 60 minutes in a dissolution test (USP apparatus I (baskets) 125 rpm, medium: phosphate buffer pH 5.5, volume 900 ml) from said dosage form.

The dosage form according to the invention may include, for instance one or more of fillers, binders, disintegrants, solubility enhancers, glidants, lubricants (if applicable, for example, if tabletting) as well as other pharmaceutical excipients. The maximum amount of excipients is typically from 50 to 60% by weight of the dosage form.

The amounts of the excipients depend on the choice of technology in question and whether the same technology, for example, granulation is used to formulate all drug substances. For example, in case wet granulation is used to formulate all drug substances then the amount of the binder is typically from about 0.1% by weight to about 50% by weight of the total weight of the dosage form.

The amount of disintegrant is typically from about 1% by weight to about 30% by weight of the total weight of the dosage form. A typical amount of a solubility enhancer is from about 1% by-weight to about 40% by weight of the total weight of the dosage form. A typical amount of a diluent or filler is from about 1% by weight to about 60% by weight of the total weight of the dosage form. A typical amount of a glidant is from about 0.1% by weight to about 20% by weight of the total weight of the dosage form. A typical amount of a lubricant is from about 0.1% by weight to about 10% by weight of the total weight of the dosage form. A typical amount of a release rate controlling excipient is from about 0.1% by weight to about 60% by weight of the total weight of the dosage form. A typical amount of a co-processed excipient is from about 1% by weight to about 60% by weight of the total weight of the dosage form.

In one embodiment the dosage form according to the invention comprises a diluents or a filler which may be used e.g. as a processing aid. The diluents or filler may be, for instance one or more of calcium carbonate (Barcroft, Cal-Carb, CalciPure, Destab, MagGran, Millicarb, Pharma-Carb, Precarb, Sturcal, Vivapres Ca), calcium phosphate, dibasic anhydrous (A-TAB, Di-Cafos A-N, Emcompress Anhydrous, Fujicalin), calcium phosphate, dibasic dihydrate (Cafos, Calipharm, Calstar, Di-Cafos, Emcompress), calcium phosphate tribasic (Tri-Cafos, TRI-CAL WG, TRI-TAB), calcium sulphate (Destab, Drierite, Snow White, Cal-Tab, Compactrol, USG Terra Alba), cellulose powdered (Arbocel, Elcema, Sanacel, Solka-Floc), silicified microcrystalline cellulose (ProSolv), cellulose acetate, compressible sugar (Di-Pac), confectioner's sugar, dextranes (Candex, Emdex), dextrin (Avedex, Caloreen, Crystal Gum, Primogran W), dextrose (Caridex, Dextrofin, Lycadex PF, Roferose, Tab fine D-IOO), fructose (Advantose, Fructamyl, Fructofin, Krystar), kaolinLion, Sim 90), lactitol (Finlac ACX, Finlac DC, Finlac MCX) lactose (Aero Flo 20, Aero Flo 65, Anhydrox, CapsuLac, Fast-Flo, FlowLac, GranuLac, InhaLac, Lactochem, Lactohale, Lactopress, Microfine, Microtose, Pharmatose, Prisma Lac, Respitose, SacheLac, SorboLac, Super-Tab, Tablettose, Wyndale, Zeparox), magnesium carbonate, magnesium oxide (MagGran MO), isomalt (Galen IQ, Isomaltidex, Palatinit), maltodextrin (C*Dry MD, Glucidex, Glucodry, Lycatab DSH, Maldex, Maltagran, Maltrin, Maltrin QD, Paselli MD 10 PH, Star-Dri), maltitol (C*PharmMaltides, Maltisorb, D-maltitol, Maltit, Amalty, Malbit) maltose (Advantose 100), mannitol (Mannogem, Pearlitol), microcrystalline cellulose (Avicel PH, Celex, Celphere, Ceolus KG, Emcocel, Ethispheres, Fibrocel, Pharmacel, Tabulose, Vivapur), polydextrose (Litesse), simethicone (Dow Corning Q7-2243 LVA, Cow Corning Q7-2587, Sentry Simethicone), sodium alginate (Kelcosol, Keltone, Protanal), sodium chloride (Alberger), sorbitol (Liponec 70-NC, Liponic 76-NC, Meritol, Neosorb, Sorbifin, Sorbitol Instant, Sorbogem), starch (Aytex P, Fluftex W, Instant Pure-Cote, Melojel, Meritena Paygel 55, Perfectamyl D6PH, Pure-Bind, Pure-Cote, Pure-Dent, Pure-Gel, Pure-Set, Purity 21, Purity 826, Tablet White), pregelatinized starch (Instastarch, Lycatab C, Lycatab PGS, Merigel, National 78-1551, Pharma-Gel, Prejel, Sepistab ST 200, Spress B820, Starch 1500 G, Tablitz, Unipure LD, Unipure WG220), sucrose, trehalose and xylitol (Klinit, Xylifm, Xylitab, Xylisorb, Xylitolo).

In one embodiment the dosage form of the invention comprises a binder. The binder may be, for instance one or more of following: acacia, alginic acid (Kelacid, Protacid, Satialgine H8), carbomer (Acritamer, Carbopol, Pemulen, Ultrez), carboxymethylcellulose sodium (Akucell, Aquasorb, Blanose, Finnfix, Nymcel, Tylose), ceratonia (Meyprofleur), cottonseed oil, dextrin (Avedex, Caloreen, Crystal Gum, Primogran W), dextrose (Caridex, Dextrofm, Lycedex PF, Roferose, Tabfme D-IOO), gelatin (Cryogel, Instagel, Solugel), guar gum (Galactosol, Meprogat, Meyprodor, Meyprofm, Meyproguar), hydrogenated vegetable oil type I (Akofine, Lubritab, Sterotex, Dynasan P60, Softisan 154, Hydrocote, Lipovol, HS-K, Sterotex HM), hydroxyethyl cellulose (Alcoramnosan, Cellosize, Idroramnosan, Liporamnosan, Natrosol, Tylose PHA), hydroxyethylmethyl cellulose (Culminal, Tylopur MH, Tylopur MHB, Tylose, MB, Tylose MH, Tylose MHB), hydroxypropyl cellulose (Klucel, Methocel, Nisso HPC), low substituted hydroxypropyl cellulose, hypromellose (Benecel MHPC, Methocel, Metolose, Pharmacoat, Spectracel 6, Spectracel 15, Tylopur), methylcellulose (Benecel, Culminal MC), magnesium aluminium silicate (Carrisorb, Gelsorb, Magnabite, Neusilin, Pharmsorb, Veegum), maltodextrin (C*Dry, MD, Glucidex, Glucodry, Lycatab DSH, Maldex, Maltagran, Maltrin, Maltrin QD, Paselli MD 10 PH, Star-Dri) maltose (Advantose 100), methylcellulose (Benecel, Culminal MC, Methocel, Metolose), microcrystalline cellulose (Avicel PH, Celex, Celphere, Ceolus KG, Emcocel, Ethispheres, Fibrocel, Pharmacel, Tabulose, Vivapur), polydextrose (Litesse), polyethylene oxide (Polyox), polymethacrylates (Eastacryl 300, Eudragit, Kollicoat MAE 30D, Kollicoat MAE 30DP), povidone (Kollidon, Plasdone), sodium alginate (Kelcosol, Keltone, Protanal), starch (Aytex P, Fluftex W, Instant Pure-Cote, Melojel, Meritena Paygel 55, Perfectamyl D6PH, Pure-Bind, Pure-Cote, Pure-Dent, Pure-Gel, Pure-Set, Purity 21, Purity 826, Tablet White), pregelatinized starch (Instastarch, Lycatab C, Lycatab PGS, Merigel, National 78-1551, Pharma-Gel, Prejel, Sepistab ST 200, Spress 8820, Starch 1500 G, Tablitz, Unipure LD, Unipure WG 220), stearic acid (Crodacid, Emersol Hystrene, Industrene, Kortacid 1895, Pristerene), sucrose and zein.

In one embodiment of the invention the binder is a binder suitable for use in hot melt granulation (hot melt binder). Such a binder may be, for example one or more of the following: Polyethylene glycol (Breox PEG, Carbowax, Hodag PEG, Lutrol E), Stearic acid, Paraffin, Castor oil, hydrogenated (Castorwax, Castorwax MP 70, Castorwax MP 80, Opalwax, Sinulsol), Carnauba wax, Candelilla wax, Cottonseed oil, hydrogenated (Lubritab, Sterotex), glyceryl monostearate (Advawax 140, Atmul 67, Citomulgin M, Estol 603, Hodag GMS, Myvaplex 600P), acetylated glycerol monostearate, sorbitan monostearate (Capmul S, Liposorb S, Protachem SMS, Span 60), hexadecyl palmitate, octadecyl stearate, glyceryl trimyristate (Dynasan 114), glyceryl trilaurate (Dynasan 112), glyceryl tripalmitate (Dynasan 116), glyceryl tristearate (Dynasan 118) and glyceryl behenate (Compritol 888 Ato).

In one embodiment the dosage form according to the invention comprises a disintegrant. The disintegrant maybe, for instance one or more of following: alginic acid (Kelacid, Protacid, Satialgine H8), calcium phosphate, tribasic (Tri-Cafos, TRI-CAL WG, TRI-TAB), carboxymethylcellulose calcium (ECG 505, Nymcel ZSC), carboxymethylcellulose sodium (Akucell, Aquasorb, Blanose, Finnfix, Nymcel Tylose CB), colloidal silicon dioxide (Aerosil, Cab-O-Sil, Cab-O-Sil M-5P, Wacker HDK), croscarmellose sodium (Ac-Di-Sol, Explocel, Nymcel ZSX, Pharmacel XL, Primellose, Solutab, Vivasol), crospovidone (Kollidon CL, Kollidon CL-M, Polyplasdone XL, Polyplasdone XL-IO), docusate sodium, guar gum (Galactosol, Meprogat, Meyprodor, Meyprofin, Meyproguar), low substituted hydroxypropyl cellulose, magnesium aluminun silicate (Carrisorb, Gelsorb, Magnabite, Neusilin, Pharmsorb, Veegum), methylcellulose (Benecel, Culminal MC, Methocel, Metolose), microcrystalline cellulose (Avicel PH, Celex, Celphere, Ceolus KG, Emcocel, Ethispheres, Fibrocel, Pharmacel, Tabulose, Vivapur), povidone (Kollidon, Plasdone) sodium alginate (Kelcosol, Keltone, Protanal), sodium starch glycolate (Explotab, Primojel, Vivastar P), polacrilin potassium (Amberlite IRP88), silicified microcrystalline cellulose (ProSolv), starch (Aytex P, Fluftex W, Instant Pure-Cote, Melojel, Meritena, Paygel 55, Perfectamyl D6PH, Pure-Bind, Pure-Cote, Pure-Dent, Pure-Gel, Pure-Set, Purity 21, Purity 826, Tablet White) or pregelatinized starch (Instanstarch, Lycatab C, Lycatab PGS, Merigel, National 78-1551, Pharma-Gel, Prejel, Sepistab ST 200, Spress B820, Starch 1500 G, Tablitz, Unipure LD and Unipure WG220).

In one embodiment the dosage form according to the invention comprises a solubility enhancer. The solubility enhancer may be, for instance one or more of the following: cyclodextrins (Cavitron, Encapsin, Rhodocap, Kleptose), glyceryl monostearate (Abracol SLG, Admul, Myvaplex 600P), lecithin, poloxamer (Lutrol, Monolan, Pluronic), polyoxyethylene fatty acid esters (polysorbates) (Tween), polyoxyethylene castor oil derivatives (Cremophor series), docusate sodium (Cropol), sodium lauryl sulphate (Elfan 240, Maprofix 563), sorbitan esters (sorbitan fatty acid esters) (Span), polyvinyl pyrrolidone, polyethylene glycol (PEG), lauryl macrogol glyceride (Gelucire) and d-alpha-tocophenyl PEG succinate (Vitamin E TPGS NF).

In one embodiment the dosage form according to the invention comprises a release rate controlling excipient. The release controlling excipient may be, for instance one or more of hydroxypropyl cellulose, hypromellose, hydroxy ethyl cellulose, ethyl cellulose, cellulose ethers, poly(ethylene oxide), microcrystalline cellulose, carbomer, carbomers, carbomer copolymer, povidone (Kollidon, Plasdone) polyvinyl acetate-povidone (Kollidon SR), fatty acids, fatty acid esters, magnesium stearate, calcium stearate, stearic acid, stearyl alcohol, glyceryl monostearate (Capmul GMS-50, Cutina GMS, Imwitor 191 and 900, Kessco GMS5 Lipo GMS 410, 450 and 600, Myvaplex 600P, Myvatex, Protachem GMS-450, Rita GMS, Stepan GMS, Tegin, Tegin 503 and 515, Tegin 4100, Tegin M, Unimate GMS), glyceryl behenate (Compritol 888 ATO), glyceryl palmitostearate Precirol ATO 5) hydrogenated castor oil (Castorwax, Castorwax MP 70, Castorwax MP 80, Croduret, Cutina HR, Fancol, Simulsol 1293), hydrogenated vegetable oil type I (Akofine, Lubritab, Sterotex, Dynasan P60, Softisan 154, Hydrocote, Lipovol HS-K, Sterotex HM), carnauba wax, shellac, rosin, zein, traganth gum, xanthan gum, guar gum, locust bean gum (Ceratoria). Other examples of suitable polymers include (but are not limited to) cellulose acetate, cellulose acetate phthalate, hypromellose phthalate, hypromellose acetate succinate, polyvinyl acetate, polyvinyl acetate phthalate, alginic acid and its salts like sodium alginate, potassium alginate, calcium alginate, propylene glycol alginate. Also a release rate controlling agent may be acrylic acid polymers and copolymers like methyl acrylate, ethyl acrylate, methyl methacrylate and/or ethyl methacrylate with copolymers of acrylic and methacrylic acid esters (Eudragit NE, Eudragit RL, Eudragit RS, Eudragit FS30D, Eudragit L, Eudragit S, Eudragit S100, Eudragit L100-55, RS30D, RL30D, NE30 D, Kollicoat MAE 30D, Kollicoat MAE 30DP, Acryl EZE, Acryl EZE-MP, Eastacryl 30D) and the like and any mixture or combination thereof, cellulose acetate, cellulose diacetate, cellulose triacetate, cellulose acetate phthalate, polyvinyl acetate phthalates, hydroxypropyl methylcellulose phthalates, hydroxypropyl methylcellulose acetate succinates LF, hydroxypropyl methylcellulose acetate succinate HF, and others.

In one embodiment the dosage form according to the invention comprises a glidant. The glidant may be, for instance one or more of the following: tribasic calcium phosphate (Tri-Cafos, TRI-CAL, TRI-TAB), calcium silicate, cellulose, powdered (Arbocel, Elcema, Sanacel, Solka-Floc), colloidal silicon dioxide (Aerosil, Cab-O-Sil, Cab-O-Sil M-5P, Wacker HDK), magnesium silicate, magnesium trisilicate, starch (Aytex P, Fluftex W, Instant Pure-Cote, Melojel, Meritena, Paygel 55, Perfectamyl D6PH, Pure-Bind, Pure-Cote, Pure-Dent, Pure-Gel, Pure-Set, Purity 21, Purity 828, Tablet White) and talc (Altalc, Luzenac, Luzenac Pharma, Magsil Osmanthus, Magsil Star, Superiore).

In one embodiment the dosage form is a tablet or a core tablet and a lubricant may be used to improve the tabletting. The lubricant may be for instance one or more of following: calcium stearate (HyQual), glycerine monostearate (Capmul GMS-50, Cutina GMS, Imwitor 191 and 900, Kessco GMS5 Lipo GMS 410, 450 and 600, Myvaplex 600P, Myvatex, Protachem GMS-450, Rita GMS, Stepan GMS, Tegin, Tegin 503 and 515, Tegin 4100, Tegin M, Unimate GMS), glyceryl behenate (Compritol 888 ATO), glyceryl palmitostearate Precirol ATO 5), hydrogenated castor oil (Castorwax, Castorwax MP 70, Castorwax MP 80, Croduret, Cutina HR, Fancol, Simulsol 1293), hydrogenated vegetable oil type I (Akofine, Lubritab, Sterotex, Dynasan P60, Softisan 154, Hydrocote, Lipovol HS-K, Sterotex HM), magnesium lauryl sulphate, magnesium stearate, medium-chain triglycerides (Captex 300, Captex 355, Crodamol GTC/C, Labrafac CC, Miglyol 810, Miglyol 812, Myritol, Neobee M5, Nesatol, Waglinol 3/9280), poloxamer (Lutrol, Monolan, Pluronic, Supronicm, Synperonic), polyethylene glycol (Carbowax, Carbowax Sentry, Lipo, Lipoxol, Lutrol E, Pluriol E), sodium benzoate (Antimol), sodium chloride (Alberger), sodium lauryl sulphate (Elfan 240, Texapon KI 2P), sodium stearyl fumarate (Pruv), stearic acid (Crodacid E570, Emersol, Hystrene, Industrene, Kortacid 1895, Pristerene), talc (Altalc, Luzenac, Luzenac Pharma, Magsil Osmanthus, Magsil Star, Superiore), sucrose stearate (Surfhope SE Pharma D-1803 F) and zinc stearate (HyQual).

In one embodiment the dosage form according to the invention comprises as co-processed excipients any combinations of these components which by their functions for improv said properties. Some of them are commercially available like cellulose and silicified microcrystalline (ProSolv) or microcrystalline cellulose-silicon dioxide-sodium starch glycolate and sodium stearyl fumarate (ProSolv EASYtab).

In one embodiment of the invention the tablet, minitablet, granule and/or the pellet disclosed herein may be coated. In one embodiment of the invention the coating comprises one or more of the following polymers: a cellulose derivative, polyvinyl alcohol, polyethylene glycols, acrylate polymers or a sugar derivative. Preferably, a water based coating is used. The coating may comprise plasticizers, dyes, colour lakes, or pigments, such as iron oxides, for instance yellow or red irons oxides and titanium dioxide.

Entacapone used in the dosage form of the invention is preferably a substantially pure (E)-isomeric form the preparation of which has been disclosed in U.S. Pat. No. 5,135,950. The (E)-isomer may take different polymorphic forms, e.g. polymorph A disclosed in U.S. Pat. No. 5,135,950 or polymorph D disclosed in WO 2005/063696.

The water solubility of entacapone is rather slow. Due to poor solubility, the dissolution rate of entacapone can be a limiting factor for the absorption of entacapone in the gastrointestinal tract. WO 2006/131591 discloses that in order to facilitate the absorption, entacapone having reduced particle size (i.e. at least 90% of entacapone particles have a diameter less than 55 microns e.g. less than 35 microns) is preferably used when making granules comprising entacapone. The specific surface area (SSA) of such fine particles of entacapone is typically higher than 2.0 m$^2$/g.

Thus, in one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from: 1.0 to 3.08:1.0 by weight, is provided, wherein in the preparation of said dosage form entacapone has been used having specific surface area of from 2 m$^2$/g to 20 m$^2$/g.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided, wherein in the preparation of said dosage form entacapone has been used having specific surface area of from 2.2 m$^2$/g to 7 m$^2$/g.

Entacapone particles of reduced particle size, however, have tended to cause manufacturing problems. Potential problems related to fine particle size include poor flowability and agglomeration which may result in compromised content uniformity (i.e. the reproducible amount of entacapone between different units). The use of coarser particle size would therefore be beneficial. Such a coarser particle size could be used, for example, in direct compression which is advantageous, as direct compression is an inexpensive and efficient manufacturing process. It has now been surprisingly found out by the applicants that is not necessary (but it is still possible) to use such a small particle size of entacapone when preparing the dosage forms according to the invention. Quite to the contrary, when using particle sizes of entacapone larger than the ones disclosed in WO 20061/131591 it is possible to influence the pharmacokinetic profile of levodopa by reducing the time to Cmax i.e. Tmax. Reduced Tmax could be highly valuable to a patient who has troublesome early-morning parkinsonian symptoms such as akinesia, rigidity and foot dystonia.

Thus, in one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided, wherein in the preparation of said dosage form entacapone has been used having specific surface area of from 0.2 m$^2$/g to less than 2 m$^2$/g. Entacapone particles having a SSA from 0.2 m$^2$/g to 2 m$^2$/g are considered to consist mainly of medium sized particles.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided, wherein in the preparation of said dosage form entacapone has been used having specific surface area of from 0.2 m$^2$/g to 1.0 m$^2$/g.

Still in another embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided, wherein in the preparation of said dosage form entacapone has been used having specific surface area of from 0-01 to less than 0.2 m$^2$/g. Entacapone particles having a SSA from 0.01 m$^2$ to 0-2 m$^2$ are considered to consist mainly of coarse sized particles.

The particle size of levodopa for use in the dosage form of the present invention may be a particle size as typically used in formulations comprising levodopa. The particle size of commercially available levodopa may generally be suitable.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided, wherein in the preparation of said dosage form entacapone has been used having specific surface area of from 0.1 to 0.2 m$^2$/g.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided, wherein in the preparation of said dosage form levodopa has been used having specific surface area of from 0.1 to 1.0 m$^2$/g.

The particle size of carbidopa for use in the dosage form of the present invention may be a particle size as typically used in formulations comprising carbidopa.

In one embodiment of the invention a method for the preparation of a oral solid dosage form comprising
(i) levodopa in an amount ranging from 50 mg to 200 mg,
(ii) carbidopa in an amount ranging from 65 mg to 150 mg or a therapeutically equivalent amount of another aromatic amino acid decarboxylase inhibitor, and
(iii) entacapone in an amount ranging from 100 mg to 200 mg, wherein the proportion of entacapone to carbidopa in said dosage form ranges from 0.66:1.0 to 3.08:1.0 by weight, is provided, wherein in the preparation of said dosage form carbidopa has been used having specific surface area of from 0.5 to 10 m$^2$/g.

The SSA values are measured using three-point nitrogen gas adsorption according to the BET (Brunauer-Emmett-Teller) technique well known in the art (e.g. using Coulter SA3100, Coulter Corp. or TriStar 3000, Micromeritics, or other corresponding equipment).

The entacapone particles used in the dosage form(s) as well as in the preparation thereof according to this disclosure can be produced by any method used in the art for obtaining particles with a desired specific surface area and/or particles size distribution. Thus, they may be obtained directly from the production scale processes (e.g. by direct crystallization) or reducing the particle size of said entacapone particles for example mechanically (e.g. by milling, for instance by a ball mill, a fluid energy attrition mill or a jet mill), by ultrasonic means and/or by fractionating. As a general textbook reference on providing particles of desired size as well as to manufacturing technologies mentioned herein a reference is made to Remington's Pharmaceutical Sciences, $18^{th}$ ed, 1990, Mack Publishing Company, Easton, Pa. 18042. Suitable manufacturing technologies may be also found in Pharmaceutics the Science of Dosage Form Design Ed. M. E. Aulton, 2000.

The particle size of aromatic amino acid decarboxylase inhibitor other than carbidopa and of COMT inhibitor other than entacapone may similarly be the size typically used in formulations comprising these substances, and commercially available materials may be of a suitable particle size.

It is to be understood that whenever a method for the preparation a given dosage form is mentioned herein in the context of this disclosure it is meant that this invention also comprises the dosage forms obtainable using said method. Thus, the present invention also relates to dosage forms, particularly oral solid dosage forms, including single unit dosage forms and multiple-unit dosage forms, comprising granules, tablets, minitablets, pellets, capsules, sachets or dispensers obtainable by the methods described above. It is further to be understood that any specific disclosure herein regarding amounts, ranges, excipients, particle size, manner of formulation, parameters, etc may be applied, as would be evident to the skilled person, to any embodiment disclosed herein whether methods (e.g., methods for the treatment of the body or methods of manufacture) or products, e.g. dosage forms.

The present disclosure also provides a kit for simultaneous or sequential administration of levodopa, carbidopa or a therapeutically equivalent amount of another aromatic amino acid decarboxylase inhibitor, and entacapone, a moderately potent COMT inhibitor, or a highly potent COMT inhibitor in the amounts described above. The kit may comprise the levodopa, aromatic amino acid decarboxylase inhibitor (such as carbidopa) and COMT inhibitor (such as entacapone) in any combination. Thus, the kit may suitably be comprised of oral solid dosage forms in any combination of single and multi-unit dosage forms as defined above. Thus, in one embodiment, a kit may be comprised of all single oral dosage forms as defined above. For example, such a kit might comprise a number of tablets, each of which comprise levodopa, carbidopa and entacapone, for individual administration at set time intervals.

In another embodiment, a kit may be comprised of all multi-unit dosage forms in the form of individual tablets containing the drug substances. By way of example, such a kit could comprise entacapone in one tablet and a separate tablet containing levodopa and carbidopa for sequential administration. In a further embodiment, a kit may comprise multi-unit dosage forms in the form of a plurality of oral solid units (i.e. multiple unit or multi-particulate dosage forms), e.g. a capsule, sachet or dispenser filled with minitablets, granules or pellets. In another embodiment, a kit may comprise one or more single oral dosage forms and one or more multi-unit dosage forms. Thus, a further example of a kit may comprise (1) a single oral dosage form comprising a COMT inhibitor, levodopa and carbidopa and (2) further oral solid dosage forms (single oral dosage forms or multi-unit dosage forms) for separate administration which comprise levodopa and carbidopa and optionally the same COMT inhibitor or a different COMT inhibitor, such as entacapone.

The present disclosure will be illustrated by the following non-limiting examples.

EXAMPLES

Example 1

The primary objective of the study was to evaluate the effects of different carbidopa dose levels on the pharmacokinetics (PKs) of levodopa with and without concomitant administration of entacapone. This was the first study to evaluate the effect of the combinations in a repeated dose setting in human subjects. Pharmacokinetics of levodopa in the presence of AADC and COMT inhibition with substances like carbidopa and entacapone is complex and difficult to model based on single dose PK data in humans, or animal models. However, it has been shown earlier that levodopa PK in healthy subjects is similar to that seen in PD patients and therefore the results of this study indicate how the levodopa PK will be in PD patients and how the levodopa PK will predict symptom control of PD.

A total of 25 human subjects were enrolled into the study. The study subjects were randomly allocated to receive either 200 mg of entacapone or corresponding placebo in each treatment period. Entacapone, or a corresponding placebo, was administered concomitantly with 100 mg of levodopa and 25 mg of carbidopa at 3.5-hour intervals 4 times a day. In addition, the study subjects received in a randomised order in each treatment period one of the additional dose levels (0 mg, 25 mg, and 75 mg) of carbidopa.

There were 3 treatment periods, one for each carbidopa dose level and for the same subjects with cross-over design so that each subject participated for the 3 periods. There were two groups with the same carbidopa doses, one group with and one group without concomitant entacapone administration. By this study design, the effect of entacapone on carbidopa dose escalation and subsequently to levodopa PK could be assessed in repeated dose setting in humans.

Figure 2:
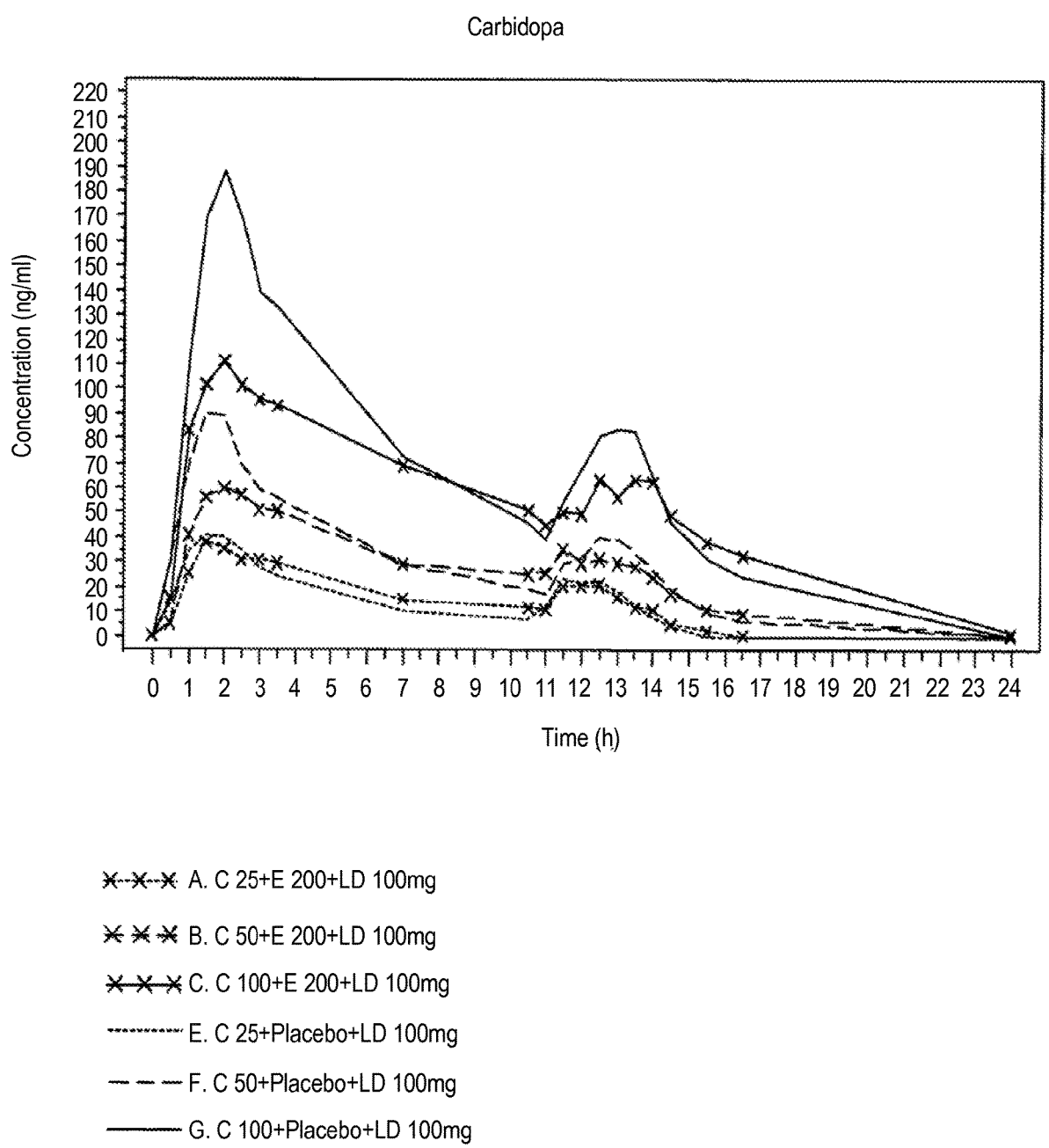
FIG. 2 shows the mean carbidopa plasma concentrations (ng/ml) by study treatments:
A: Entacapone 200 mg+levodopa 100 mg+carbidopa 25 mg
B: Entacapone 200 mg+levodopa 100 mg+carbidopa 50 mg
C: Entacapone 200 mg+levodopa 100 mg+carbidopa 100 mg
E: Levodopa 100 mg+carbidopa 25 mg
F: Levodopa 100 mg+carbidopa 50 mg
G: Levodopa 100 mg+carbidopa 100 mg.

Dose Combinations were:
A: Entacapone 200 mg+levodopa 100 mg+carbidopa 25 mg
B: Entacapone 200 mg+levodopa 100 mg+carbidopa 50 mg
C: Entacapone 200 mg+levodopa 100 mg+carbidopa 100 mg
E: Levodopa 100 mg+carbidopa 25 mg
F: Levodopa 100 mg+carbidopa 50 mg
G: Levodopa 100 mg+carbidopa 100 mg After the first and last dose of the day, the whole levodopa and carbidopa plasma profiles were assessed and after the second and third dose only the minimum concentrations (just before the next dose at 3.5 and at 7.0 hours) were assessed. The results concerning levodopa are given in FIG. 1 and the results concerning carbidopa are given in FIG. 2.

The results demonstrate that in repeated dosing regimen, and with the presence of entacapone, increasing the carbidopa dose will significantly improve levodopa pharmacokinetics in human subjects. Without entacapone, the carbidopa dose increase did not have such an effect. This means that changing the ratios of the three concomitantly (i.e. simultaneously) or sequentially administered drugs, levodopa pharmacokinetics and subsequently treatment of signs and symptoms of Parkinson's disease can be significantly improved

Example 2

The primary objective of the study was to evaluate the effects of different carbidopa dose levels on the pharmacokinetics (PKs) of levodopa with concomitant administration of different entacapone dose levels and with the moderately potent COMT inhibitor tolcapone.

The study subjects were randomly allocated to receive either increasing doses of entacapone or standard dose of tolcapone combined with increasing doses of carbidopa in each treatment period, a total of 12 different dose combinations. Entacapone was administered concomitantly with 100 mg of levodopa and 25 mg of carbidopa at 3.5-hour intervals 4 times a day and tolcapone 3 times a day. In addition, the study subjects received increasing dose levels of carbidopa.

There were three groups, one for each carbidopa dose level, and 4 treatment periods in each group, one for each entacapone dose level or for tolcapone and for the same subjects with cross-over design so that one subject participated for the 4 periods. By this study design the effect of entacapone and tolcapone on carbidopa dose escalation and subsequently to levodopa PK could be assessed in repeated dose setting in humans.

Figure 3:
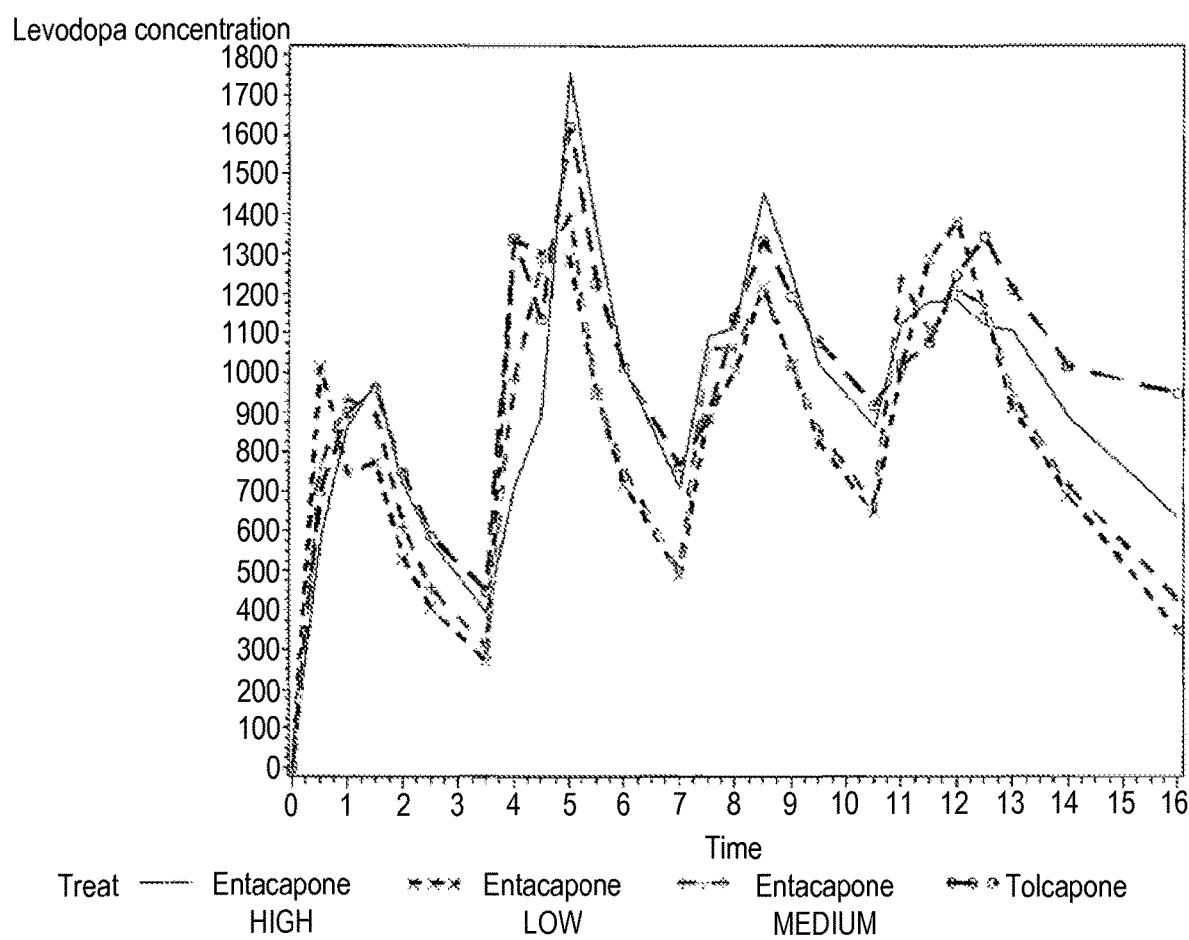
FIG. 3 shows mean levodopa concentrations in human with increased carbidopa dose and with increasing COMT-inhibition either by increasing the entacapone dose or by using the moderately potent COMT inhibitor, tolcapone.

After each levodopa dose of the day, the levodopa plasma profile was assessed. The levodopa plasma concentrations after entacapone dose escalation and tolcapone standard dose and with increased carbidopa dose are given in FIG. 3.

The results demonstrate that in repeated dosing regimen, and with the increased COMT-inhibition either by increasing the COMT-inhibitor dose or by using a more potent COMT-inhibitor, increasing the carbidopa dose will significantly improve levodopa pharmacokinetics in human subjects. This means that changing the ratios of the three concomitantly (i.e. simultaneously) or sequentially administered drugs, levodopa pharmacokinetics and subsequently treatment of signs and symptoms of Parkinson's disease can be significantly improved.

Example 3

The examples of suitable entacapone/levodopa/carbidopa tablet formulations are described in Tables 1 to 2 (formulations 1 to 4). The tablets are prepared by adding carbidopa separately as granules into the formulation. Accordingly, entacapone and levodopa are granulated together with maize starch, mannitol, croscarmellose sodium and povidone in a high shear mixer. Carbidopa is wet granulated separately with maize starch, mannitol, croscarmellose sodium, and povidone in a high shear mixer. The dry entacapone/levodopa granules, the dry carbidopa granules, croscarmellose sodium, mannitol (and castor oil, hydrogenated, in formulations 3 to 4), and magnesium stearate are mixed together and the mass obtained are compressed to tablets and coated with HPMC-coating containing a color pigment.

TABLE 1

Proposed dosage forms of entacapone/levodopa/carbidopa 100/100/80 (Formulation 1) and 200/100/80 (Formulation 2) tablet.

| Core tablet: | Formulation 1 mg/tablet | Formulation 2 mg/tablet |
| --- | --- | --- |
| Entacapone | 100.0 | 200.0 |
| Levodopa | 100.0 | 100.0 |
| Carbidopa monohydrate (corresponds to anhydrite 80.0 mg) | 86.5 | 86.5 |
| Maize starch | 77.0 | 107.0 |
| Mannitol | 141.3 | 159.7 |
| Croscarmellose sodium | 24.3 | 31.4 |
| Povidone | 32.4 | 47.9 |
| Magnesium stearate | 8.5 | 10.5 |
| Theoretical weight of the core tablet | 570.0 | 743.0 |
| HPMC-coating containing color pigments | 17.0 | 21.0 |
| Theoretical weight of the coated tablet | 587.0 | 764.0 |

TABLE 2

Proposed dosage forms of entacapone/levodopa/carbidopa 100/100/80 (Formulation 3) and 200/100/80 (Formulation 4) tablet.

| Core tablet: | Formulation 3 mg/tablet | Formulation 4 mg/tablet |
| --- | --- | --- |
| Entacapone | 100.0 | 200.0 |
| Levodopa | 100.0 | 100.0 |
| Carbidopa monohydrate (respond carbidopa 80.0 mg) | 86.5 | 86.5 |
| Maize starch | 77.0 | 107.0 |
| Mannitol | 152.7 | 173.7 |
| Croscarmellose sodium | 12.9 | 17.4 |
| Castor oil, hydrogenated | 3.0 | 4.0 |
| Povidone | 32.4 | 47.9 |
| Magnesium stearate | 8.5 | 10.5 |
| Theoretical weight of the core tablet | 573.0 | 747.0 |
| HPMC-coating containing color pigments | 17.0 | 21.0 |
| Theoretical weight of the coated tablet | 590.0 | 768.0 |

We claim:

1. A method for the treatment of Parkinson's disease comprising simultaneously or sequentially orally administering to a patient in need of treatment of Parkinson's disease
   (i) levodopa in an amount ranging from 75 mg to 175 mg,
   (ii) carbidopa in an amount ranging from 65 mg to 105 mg, and
   (iii) entacapone in an amount ranging from 100 mg to 200 mg, wherein the proportion of entacapone to carbidopa ranges from 0,95:1.0 to 3.08:1.0 by weight, and wherein the total number of doses administered per day of each of levodopa, carbidopa, and entacapone ranges from 3 to 10.

2. The method according to claim 1, wherein said treatment comprises administering orally an oral solid dosage form.

3. The method according to claim 1, wherein the proportion of entacapone to carbidopa ranges from 1.90:1.0 to 3.08:1.0 by weight.

4. The method according to claim 1, wherein entacapone is present in an amount of 100 mg, 150 mg, or 200 mg.

5. The method according to claim 4, wherein entacapone is present in an amount of 200 mg.

6. The method according to claim 1, wherein carbidopa is present in an amount of 65 mg, 80 mg, 85 mg, or 105 mg.

7. The method according to claim 6, wherein carbidopa is present in an amount of 65 mg.

8. The method according to claim 6, wherein carbidopa is present in an amount of 85 mg.

9. The method according to claim 6, wherein carbidopa is present in an amount of 105 mg.

10. The method according to claim 1, wherein the proportion of entacapone to carbidopa is 0,95:1.0, 1.18:1.0, 1.33:1.0, 1.54:1.0, 1.6:1.0, 1.9:1.0, 2.35:1.0, 2.5:1.0, or 3.08:1.0 by weight.

11. The method according to claim 1, wherein the proportion of entacapone and carbidopa is 100 mg:105 mg, 100 mg:85 mg, 100 mg:80 mg, 100 mg:65 mg, 200 mg:105 mg, 200 mg:85 mg, 200 mg:80 mg, or 200 mg:65 mg.

12. The method according to claim 1, wherein levodopa is present in an amount of 75 mg, 100 mg, 125 mg or 150 mg.

13. The method according to claim 1, wherein the proportion of levodopa to carbidopa ranges from 0.71:1.0 to 2,31:1.0 by weight.

14. The method according to claim 1, wherein the proportions of levodopa, carbidopa and entacapone are 75 mg:65 mg:200 mg, 75 mg:85 mg:200 mg, 75 mg:105 mg:200 mg, 100 mg:65 mg:200 mg, 100 mg:85 mg:200 mg, 100 mg:105 mg:200 mg, 125 mg:65 mg:200 mg, 125 mg:85 mg:200 mg, 125 mg:105 mg:200 mg, 150 mg:65 mg:200 mg, 150 mg:85 mg:200 mg, or 150 mg:105 mg:200 mg.

15. The method of claim 1, wherein the patient to be treated is an adult patient with Parkinson's disease experiencing symptoms of end-of-dose wearing off.

16. The method of claim 1, wherein the total number of doses administered per day ranges from 3 to 7.

17. An oral dosage form comprising
(i) levodopa in an amount ranging from 75 mg to 175 mg,
(ii) carbidopa in an amount ranging from 65 mg to 105, and
(iii) entacapone in an amount ranging from 100 mg to 200 mg, wherein the proportion of entacapone to carbidopa ranges from 0.95:1.0 to 3.08:1.0 by weight.

18. The dosage form according to claim 17, wherein the proportion of entacapone to carbidopa in said dosage form ranges from 1.6:1.0 to 1.9:1.0 by weight.

19. The dosage form according to claim 17, wherein entacapone is present in an amount of 200 mg, 150 mg, or 100 mg.

20. The dosage form according to claim 19, wherein entacapone is present in an amount of 200 mg.

21. The dosage form according to claim 17, wherein carbidopa is present in an amount of 65 mg, 80 mg, 85 mg, or 105 mg.

22. The dosage form according to claim 17, wherein the proportion of entacapone to carbidopa in said dosage form is 1.3:1.0, 1.6:1.0, 1.9:1.0, 2.4:1.0, or 2.5:1.0 by weight.

23. The dosage form according to claim 17, wherein the proportion of entacapone and carbidopa in said dosage form is 100 mg:105 mg, 100 mg:85 mg, 100 mg:80 mg, 100 mg:65 mg, 200 mg:105 mg, 200 mg:85 mg, 200 mg:80 mg, or 200 mg:65 mg.

24. The dosage form according to claim 17, wherein levodopa is present in an amount of 75 mg, 100 mg, 125 mg or 150 mg.

25. The dosage form according to claim 17, wherein the proportion of levodopa to carbidopa in said dosage form ranges from 1.4:1.0 to 2.3:1.0 by weight.

26. The dosage form according to claim 17, wherein the proportions of levodopa, carbidopa and entacapone in said dosage form are 75 mg:65 mg:200 mg, 75 mg:85 mg:200 mg, 75 mg:105 mg:200 mg, 100 mg:65 mg:200 mg, 100 mg:85 mg:200 mg, 100 mg:105 mg:200 mg, 125 mg:65 mg:200 mg, 125 mg:85 mg:200 mg, 125 mg:105 mg:200 mg, 150 mg:65 mg:200 mg, 150 mg:85 mg:200 mg, or 150 mg:105 mg:200 mg.

\* \* \* \* \*

UNITED STATES PATENT AND TRADEMARK OFFICE
CERTIFICATE OF CORRECTION

PATENT NO. : 10,857,120 B2
APPLICATION NO. : 14/504925
DATED : December 8, 2020
INVENTOR(S) : Juha Rouru et al.

Page 1 of 1

It is certified that error appears in the above-identified patent and that said Letters Patent is hereby corrected as shown below:

In the Claims

Claim 1, Column 32, Line 53, "0,95:1.0" should read as —0.95:1.0—.

Claim 10, Column 33, Line 10, "0,95:1.0" should read as —0.95:1.0—.

Claim 13, Column 33, Line 22, "2,31:1.0" should read as —2.31:1.0—.

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*